US010245345B2

(12) United States Patent
Sevy

(10) Patent No.: US 10,245,345 B2
(45) **Date of Patent: *Apr. 2, 2019**

(54) ATOMIZATION SEPARATING AND SILENCING APPARATUS AND METHOD

(71) Applicant: Earl Vaughn Sevy, Cedar City, UT (US)

(72) Inventor: Earl Vaughn Sevy, Cedar City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,069

(22) Filed: Apr. 5, 2018

(65) Prior Publication Data

US 2018/0264159 A1 Sep. 20, 2018

Related U.S. Application Data

(60) Division of application No. 15/297,542, filed on Oct. 19, 2016, now Pat. No. 9,943,621, which is a division of application No. 14/260,520, filed on Apr. 24, 2014, now Pat. No. 9,480,769, which is a continuation-in-part of application No. 13/854,545, filed on Apr. 1, 2013, now Pat. No. 9,415,130.

(51) Int. Cl.
*A61L 9/14* (2006.01)
*A61L 9/20* (2006.01)

(52) U.S. Cl.
CPC ................ *A61L 9/14* (2013.01); *A61L 9/205* (2013.01); *A61L 2209/11* (2013.01); *A61L 2209/14* (2013.01)

(58) Field of Classification Search
CPC .................................... A61L 9/00; A61L 9/14
See application file for complete search history.

(56) References Cited

U.S. PATENT DOCUMENTS

| | | | |
|---|---|---|---|
| 904,149 | A | 11/1908 | Rachmann |
| 2,826,454 | A | 3/1958 | Coanda |
| 3,112,074 | A | 11/1963 | Green |
| 3,515,966 | A | 6/1970 | De Valroger et al. |
| 4,235,611 | A | 11/1980 | Brownell |
| 4,243,396 | A | 1/1981 | Cronenberg |

(Continued)

FOREIGN PATENT DOCUMENTS

| | | |
|---|---|---|
| JP | 2001046920 | 9/2002 |

OTHER PUBLICATIONS

Air Aroma, http://www.air-aroma.com/diffusers, webpage, not dated.

(Continued)

*Primary Examiner* — Donald R Spamer
(74) *Attorney, Agent, or Firm* — Pate Baird, PLLC

(57) ABSTRACT

A modular, integrated, combination air purification and aroma diffuser includes a UV and catalytic oxidation germicidal cell and multiple filtrations as pre-treatment of air diffusing essential oils or other liquids as ultra-fine droplets entrained in airflow into enclosed, habitable spaces. Liquid microbicide, insecticide, fumigant, or aroma therapy is kept cleaner by eradication of microbes. Comparatively larger droplets are separated out and recycled to the reservoir after initial atomization. An electrical module, between a purifier and filters upstream and a diffuser downstream, includes a pump, a fan, and a controller for both. Staged, double-eduction, triple-separation processes include a micro-cyclone for quiet, well diffused flow of ultra-fine droplets.

20 Claims, 17 Drawing Sheets

(56) References Cited

U.S. PATENT DOCUMENTS

| | | |
|---|---|---|
| 4,976,259 A | 12/1990 | Higson et al. |
| 5,029,759 A | 7/1991 | Weber |
| 5,054,477 A | 10/1991 | Terada et al. |
| 5,201,641 A | 4/1993 | Richer |
| 5,248,448 A | 9/1993 | Waldron et al. |
| 5,309,900 A | 5/1994 | Knoch et al. |
| 5,314,529 A | 5/1994 | Tilton et al. |
| 5,549,247 A | 8/1996 | Rossman et al. |
| 5,579,758 A | 12/1996 | Century |
| 5,687,710 A | 11/1997 | Ambrosio et al. |
| 5,875,774 A | 3/1999 | Clementi et al. |
| 5,922,247 A | 7/1999 | Shoham et al. |
| 6,029,913 A | 2/2000 | Stroia et al. |
| 6,236,042 B1 | 5/2001 | Kato et al. |
| 6,669,176 B2 | 12/2003 | Rock |
| D491,259 S | 6/2004 | Garrison et al. |
| D492,020 S | 7/2004 | Sevy |
| D509,893 S | 9/2005 | Sevy |
| 6,968,069 B1 | 11/2005 | Zhao |
| D520,129 S | 5/2006 | Sevy |
| D526,710 S | 7/2006 | Sevy |
| 7,407,118 B2 | 8/2008 | Sevy |
| 7,712,683 B2 | 5/2010 | Robert et al. |
| 7,878,418 B2 | 2/2011 | Sevy |
| 7,930,068 B2 | 4/2011 | Robert et al. |
| 8,001,963 B2 | 8/2011 | Giroux |
| 9,415,130 B2 | 8/2016 | Sevy |
| 2006/0008379 A1 | 1/2006 | Mielnik et al. |
| 2008/0283049 A1 | 11/2008 | Mahoney et al. |
| 2009/0297399 A1 | 12/2009 | Ryan et al. |
| 2010/0084484 A1 | 4/2010 | Sevy |
| 2013/0327323 A1 | 12/2013 | Rubin |

OTHER PUBLICATIONS

Prolitec, http://www.prolitec.com/appliances_commercial.htm, web page, not dated.
Scent Air, http://scentair.com/why-scentair-solutions/, web page, not dated.
Brandaroma, http://www.brandaroma.com/products/, web page, not dated.
$E^2$ Aroma, The scent creative experts, http://www.e2aroma.com/appliances/smart-air-maxi/, web page, not dated.
Scent Australia, makes business sense, http://www.scentaustralia.com.au/index.php/products/scent-diffuser-zephyr, web page, not dated.
Voitair, scent systems, http://www.voitair.com/scent-systems, web page, not dated.
Fragrance Machine, Aroma Machine, Scent Machines, Air Fresheners, Fragrance System, Aroma Marketing, Duftmaschine, http://www.fragrancemachine.com/, web page, not dated.

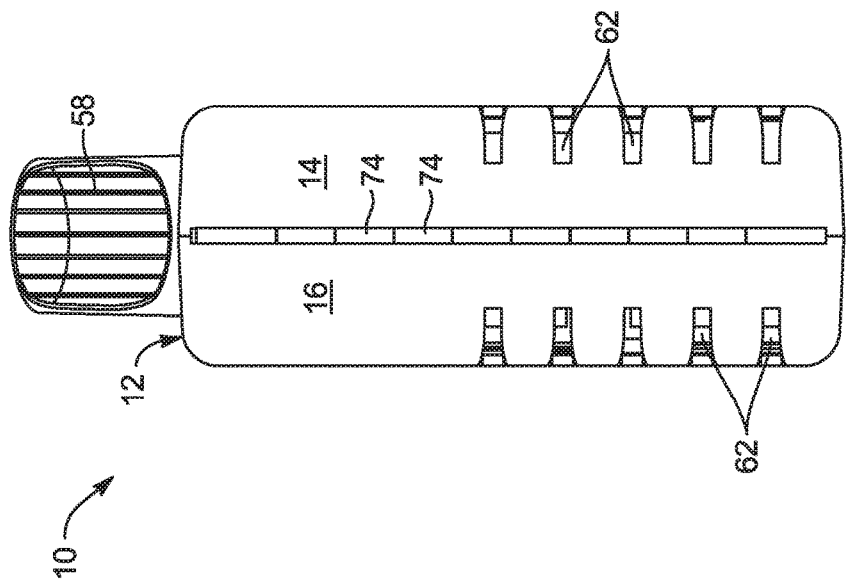
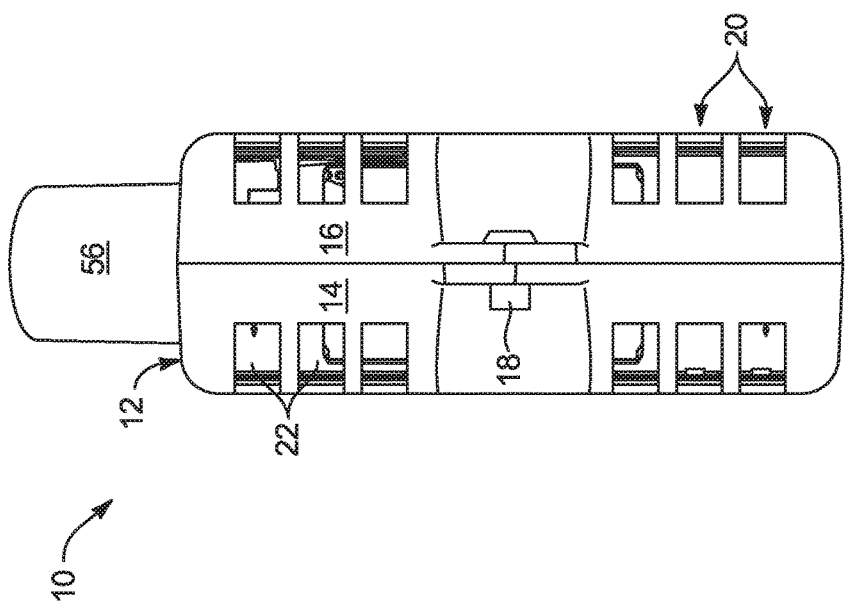

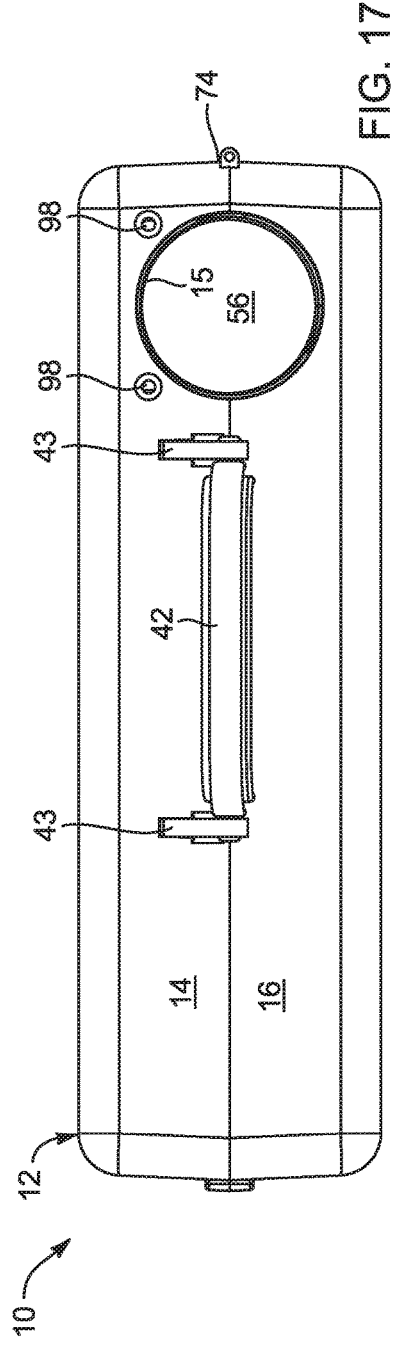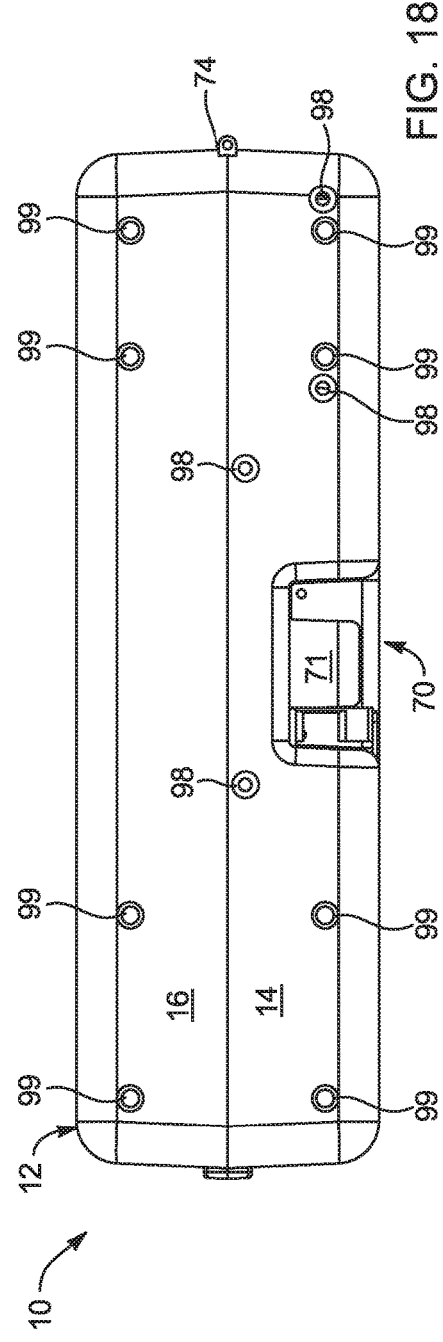

ATOMIZATION SEPARATING AND SILENCING APPARATUS AND METHOD

RELATED APPLICATIONS

This application is a divisional of U.S. patent application Ser. No. 15/297,542, filed Oct. 19, 2018; which is a divisional of U.S. patent application Ser. No. 14/260,520, filed Apr. 24, 2014, now issued as U.S. Pat. No. 9,480,769 on Nov. 1, 2016; which is a continuation-in-part of U.S. patent application Ser. No. 13/854,545, filed Apr. 1, 2013, now U.S. Pat. No. 9,415,130, issued Aug. 16, 2016; both of which are hereby incorporated by reference.

BACKGROUND

Field of the Invention

This invention relates to aroma diffusion and more particularly, to novel systems and methods for atomizing and diffusing essential oils in enclosed habitable spaces.

Background Art

Germicidal protection technology exists in sanitary industrial applications, such as restroom air germicidal protection, toilet bowl and tank purification systems, odor-control pellets, tablets, atomizers, and the like. These systems may be passive, operating strictly on vapor pressure, or maybe electrically powered, such as by heaters, lamps, fans, and the like.

Likewise, it has been found suitable to use fragrances in association with many cleaning products. These vary from kitchen soaps for dishes, to floor cleaning materials, carpet cleaners, and the like. That is, in general, it is known to put fragrances in cleaning systems. Accordingly, cleaning solvents, soaps, detergents, and the like may include fragrances leaving residual fragrance following cleaning. Nevertheless, the intention of the cleaning product itself is to either clean up "dirt" or "soil" from furniture, floors, walls, curtains, and the like, or to otherwise scrub away foreign matter.

On the other hand, disinfectants, antimicrobial materials, antiseptic materials, and the like are also used. For example, hospitals, are a case in point in which numerous germicidal liquids, vapors, pads, wipes, tools, and the like are used to wipe down surfaces, floors, restrooms, toilet facilities, sinks, and the like in order to control microbes such as germs, bacteria, viruses, and the like.

Meanwhile, an industry has developed around aromatherapy. Aromatherapy is typically directed to the infusion of an atmospheric environment, such as a room, home, kitchen, store, or the like with a scent selected from, for example, a fragrance or an essential oil, such as citrus, lavender, lemon, ginger, cinnamon, and so forth. This may be done by burning candles, heating a wax carrier that is infused with the oil, or the like. In other embodiments, essential oils may be vaporized in atomizers and distributed into a room.

Atomization creates a Gaussian distribution of droplets of a liquid entrained in a stream of air. The larger droplets tend to launch farther, once accelerated to the speed of an entraining air flow, and then drop or settle out in still air rather than remaining airborne as a fine mist would do. Thus they land on and subsequently damage furniture and other surrounding objects.

Moreover, they are less effective, evaporating more slowly because they have a lower surface-to-volume ratio than comparatively smaller droplets and mist particles.

Thus, if dispersed by an atomizer or diffuser, they may waste liquid being atomized, with less effect, while creating damage and a mess to be cleaned up.

It would be an advance in the art to provide an improved system for atomization.

BRIEF SUMMARY OF THE INVENTION

In view of the foregoing, in accordance with the invention as embodied and broadly described herein, a method and apparatus are disclosed in one embodiment of the present invention as including a system may include an electrical module, flanked by an ultraviolet germicidal module, a filtration module, and a diffuser module. In this integrated system, for example, air is drawn from an ambient surrounding the system, into the germicidal module. There, an ultraviolet light source operates directly, and on a catalytic screen to provide catalytic oxidation of live organisms, such as viruses, bacteria, and the like. Accordingly, the germicidal module draws in air, purifying that air by eradicating microbes, such as bacteria and viruses.

Meanwhile, a filtration system upstream from the germicidal module may do an initial screening for macroscopic particles, such as dust, and the like. Downstream from the germicidal module, a filtration module, or multiple filtration modules, may then capture any residual materials, such as the destroyed microbes, smaller particles of dust, and the like. In certain embodiments, the filtration module may include different types of filters, different porosities of filters, filters containing a porosity size of sieve, and the like. Otherwise, filter media such as paper, fiberglass, non woven fiber, foam, oil foam, oiled bath filaments, synthetic fiber filaments, metal filaments, coated filaments, or the like may be used as filter media in the filter module.

Downstream from the filter module is an electrical module that includes several functions. For example, a controller for operating the time, including operational cycle or duty cycle time, the delay time between operational duty time cycles, the volume of flow of an aromatic material, as well as bulk or bypass air control may be included in a control panel. Meanwhile, a display having other controls for setting up and operating a system in accordance with the invention may be provided.

The electrical module may also include a fan module for providing bulk air, most of which is bypass air. By bypass air is meant air that is not driven through a diffuser to participate in the diffusion of an aromatic liquid. Typically, the fan will provide the bulk transfer of air into the entire system, including filtration systems, as well as that passed into the diffuser system to an outlet. Typically, a small portion of that same air, treated by the germicidal module and the filtration module, will be drawn into a pump or compressor.

The entire system may be enclosed in a case suitable for use as a standing unit on a support surface, such as a shelf or floor. A handle may provide for carrying, suspending, or otherwise positioning the system overhead in a habitable space.

By habitable space is meant space that can be occupied by a living animal, such as a person, cattle, fowl, or the like. Thus, the habitable space may or may not be dwelling space. Habitable spaces may include chicken coops, other poultry sheds, cattle barns, milking parlors, rooms, halls, or the like. It is preferable in most environments to use air purification and aromatic treatment of environments in enclosed spaces, rather than wide open spaces where bulk transfer by atmospheric breezes may substantially reduce the efficiency of such a system.

In general, a case or housing around a system in accordance with the invention may be selectively openable, closable, lockable, and so forth in order to provide security, tamper-proofing, reliability, limitations on access to the controls and adjustment parameters, and so forth.

In certain embodiments, the housing may also include apertures, or relief portions that may be readily transformed into apertures by penetrating therethrough with fasteners. In certain embodiments, the relief portions are thinned wall portions that eliminate open apertures unused in the housing. These provide for creation of apertures by penetration by a fastener through a comparatively thin wall coincident with the outer surface of the housing, and provided with relief interior thereto. Thus, the hole is not a through hole, but is a very thinly walled blind hole.

In certain embodiments, the apparatus in accordance the invention may be suspended overhead, may be carried, may be set on a surface to support it, or may be mounted to a wall. In any event, the system may be used in any or all such configurations.

The pump or compressor will then compress that portion of air drawn out of the principal flow, and pass it into a diffuser. Diffusers in accordance with the invention have been described in U.S. Pat. No. 7,878,418 issued Feb. 1, 2011 to Sevy, and U.S. Pat. No. 8,047,813 issued on Nov. 1, 2011 to Sevy, both of which are hereby incorporated by reference in their entireties.

In addition to the diffuser system as described in the foregoing patent applications, with the pumps or compressors disclosed therein, a system in accordance with the invention may include an improved diffuser nozzle system including a micro-cyclone.

The micro-cyclone operates as a channel, enclosed, and spiraling upward a full height of the channel, while circumnavigating or spiraling around the internal diameter of the diffuser housing. It traverses an angular distance of from about 180 to about 400 degrees. Typically, a design set point is about 330 degrees for the total swept angle of the micro-cyclone. The micro-cyclone tends to operate as a cyclone separator to remove comparatively larger diameter, heavier droplets from the stream of entrained and diffused vapor droplets in the compressed airflow.

The micro-cyclone may have a dam operating as a baffle prior to air exit, further providing direction changes, small apertures, and the like in order to limit sound and strip off heavy droplets. It may provide a gap therein to allow backflow of any coalesced liquid that has been stripped off against a wall of the micro-cyclone or dam.

Another benefit of a system in accordance with the invention is an adapter that adapts a fitting of the diffuser to a matched fitting of a supply reservoir. Supply reservoirs and fittings may come in all types of sizes and shapes. In order to accommodate an arbitrary selection of a supply reservoir, various adapters are provided in accordance with the invention to interface with the reservoir of substantially any supplier. A user may obtain a supply of aromatic liquid from any source, and use the container therefrom, or fill a generic reservoir, fitted by the adapter to the diffuser. This improves over conventional systems that rely on canister reservoirs having integrated diffusers. These, typically, are proprietary, and lock out the ability of an owner or operator to choose a source of supply, a reservoir style or type. The invention provides an economical escape from the investment in a proprietary cartridge replacement history required to operate a diffuser.

The system described hereinabove also may include a shroud to conduct the primary or bulk airflow away from the diffuser, entraining therein, through eduction by the principal flow drawing in the diffuser flow, diffused liquid droplets. The mixed flow passes out of a directional shroud, through louvers or a grill into a habitable space.

In general, a system in accordance with the invention may operate by drawing in environmental air from an enclosed space to be treated, filtering that air initially, followed by a germicidal exposure, such as by a catalytic oxidation, an ultraviolet irradiation or both energy sources. Catalysis may occur typically on a metal plate or screen, followed by filtering through multiple filter media modules to remove residual, comparatively smaller inorganic particles, as well as destroyed microbes, and the like.

Bypassing the diffuser by a certain portion of the air flow permits cooling of electrical module containing controls, pumps, fans, and the like. A fan, for example, may be driving the principal (bulk) flow of air. The principal flow may thereby cool the motor of the fan, as well as the motors in the air pumps acting as compressors. Meanwhile, electrical controls and electronics may be cooled by the principal airflow, most of which end up bypassing the diffuser.

After cooling electrical equipment in the electrical module, the principal flow of air may pass on into a chamber that contains the diffuser module. In fact, the chamber containing the diffuser and reservoir may be considered a part of the diffuser module of the system.

Meanwhile, an extracted flow taken from the principal flow may be compressed by a pump, compressor, or the like to be passed into a diffuser. A diffuser may draw in air, or induct air into the pump, compress the air, then educt (entrain by eduction; momentum transfer) an essential oil or other liquid as comminuted (atomized) droplets, into the high speed, high pressure flow passing into a nozzle from a feed line. Following atomization, a series of baffles, including the micro-cyclone discussed above may result in a separation of the comparatively larger particles from the flow. Thus, only particles sufficiently small to flow with the airflow and not settle out for minutes remain.

Overly large particles provide a number of problems. First, they are a waste of an expensive product, the liquid, such as aromatic oil, disinfection, biocide, microbicide, fragrance, or the like. Meanwhile, they also result in too rapid a settling time in the environment. The ratio of their weight to drag forces do not result in a dwell time over a minute, or preferably five to ten minutes, or more preferably ten to thirty minutes. Thus, rather than remaining in the air, until they have evaporated or been otherwise incorporated into the atmosphere of the enclosed environment, they may instead settle out relatively quickly, onto surfaces, furniture, floors, into HVAC systems, or the like. It has been found suitable to take out the largest droplets by baffling, the micro-cyclone, and so forth.

Following this separation, eduction of the diffuser flow into the principal flow is conducted by passing the principal flow up around the diffuser, in the same direction as the diffused, liquid-droplet-laden, diffusion stream, toward a shroud for exit through an outlet. The outlet may be movable, such as rotatable, to provide for directing a stream of the principal flow of air, purified, treated with a liquid, such as an aromatic oil. The stream may be aimed in a direction to promote a long entrainment plume into a room.

For example, by providing a substantial flow, out a hydraulic diameter (hydraulic diameter is four times the area divided by the wetted perimeter of an opening) of the unit, a jet or plume may be extend a distance of over twenty outlet diameters may typically be valuable before the outgoing airstream of principal flow has decayed to insignificance.

In certain embodiments, selection of the liquid to be contained within the reservoir of the diffuser system provides additional germicidal action by the diffused liquid droplets in the enclosed, habitable space or environment. The germicidal module provides for purification of the principal flow, including air to be run through the diffuser. Meanwhile, the filtration assists in keeping a clean system without dust particles, and with no collection of live microbes in any location in the system. For example, the germicidal module is upstream from the filtration module to assure that a filtration system containing moisture and live microbes is not permitted to exist nor persist in the system.

However, downstream, the system persists in its germicidal activities when the proper liquids are selected. Antibacterial liquids, antimicrobial liquids, disinfectants, essential oils that have antimicrobial effects, or the like may be used, combined, or otherwise placed in the diffuser module. Such provide downstream antibacterial or antimicrobial activities in the treated space.

In certain embodiments, the diffusers may draw from multiple reservoirs. In other embodiments, multiple diffusers may be used in the diffusion module. Nevertheless, it has been found suitable in most environments, to use a single diffuser with a reservoir filled with a suitable liquid. That liquid may be a combined mixture of various liquids in a preselected volumetric fraction suitable to the environmental space to be treated.

A system in accordance with the invention may be used in numerous environments. For example, aroma therapists provide systems for creation of an environment associated with the therapy. The essential oil or other liquids used in the diffuser may be part and parcel of, or may be an adjunct to, a particular exercise, treatment, or the like. Similarly, massage therapists may use the system for relaxation. Naturopaths may use the system for various respiratory therapy, such as the use of eucalyptus, raven sara, rosemary, or the like. Similarly, peppermint may be used as a relaxant. Likewise, other alternatives may be used for pain or physiological treatments.

Reiki practitioners may use essential oils that are not just combinations of alcohols, phenols, and turpines, but may provide other emotional or treatment benefits. Aromatherapy enthusiasts, such as retailers and consultants for oil sales companies require a dependable method to diffuse oils in demonstrations and work environments. Likewise, cosmetologists, hospitals, as discussed above, spas, and the like may provide distribution of particular oils suited to specific needs.

For example, essential oils such as lavender, marjoram, mandarin, palo santo, may be used for relaxation of anxiety or insomnia. Similarly, antifungal agents such as niaouli, tea tree, and the like may be used for manicure or pedicure treatments. Other essential oils such as geranium, clary sage, ylang ylang, rose, jasmine, and the like may be used for mood improvements. Frankincense, lavender, helychrisum, or the like may be used for facial treatments, tissue restoration, damage prevention for tissues, free radical scavenging, and the like.

Similarly, essential oils such as peppermint, ginger, and palo santo may provide other benefits. In educational environments, atomized diffusion into classrooms may be used to make them more desirable, or to provide various responses. Typically, black pepper, cardamom, eucalyptus, peppermint, rosemary, marjoram, basil, bergamot, lemon, lemongrass, verbena, and the like may be suitable. Also, thieves' oil is considered to be a prophylactic for respiratory ailments and the like.

Meanwhile, events, retail outlets, shopping malls, casinos, grocery stores, airlines, hotels, and the like may use a system in accordance with the invention to provide a particular area with an aroma that masks other less inviting odors, tends to increase a particular state of mind among customers, or both. For example, the smell of coffee upon entrance into a retail establishment, such as a book store with a coffee shop, or a grocery store with a deli, and the like has been found to increase coffee sales by hundreds of percentage points. Likewise, scent branding specialists may use the system in order to determine the best ambient scent for anything from a retail establishment, to a car dealership, or the like.

The entertainment industry, real estate agencies, banks, veterinary hospitals, pet stores, sporting events, and the like may diffuse scents calculated and tested to provide suitable responses. Meanwhile, the entire hospitality industry is in need of suitable, reliable, easily maintainable systems to provide aromatic environments. Thus, cruise ships, airlines, ski resorts, fitness centers, amusement parks, theaters, resorts, and the like may use a system in accordance with the invention.

In certain environments, pest control may be effected. Proper selection provides a fumigation system for bed bugs, other bugs, viruses, and other microbes. For example, cedar, peppermint, clove, and lemon, have been shown to eradicate various types of bugs and pests in hotel rooms. A system in accordance with the invention with handle and feet to render it portable, allows a chamber made to effectively provide an extermination function while cleaning hotel rooms. Exterminators may find essential oils safer and nontoxic as methods as getting rid of pests using a system in accordance with invention.

Meanwhile, other processing plants, particularly food processing plants where avoidance of bacteria is important may be benefited by a system in accordance with the invention. Individual homeowners and businesses may likewise benefit. Care centers, chiropractic centers, other medical entities like hospitals, dentists, hospice sponsors, home healthcare professionals, and the like may use a system in accordance with the invention to provide essential oil treatments, medical treatments, environmental germicidal treatments, and the like.

Medication processes, trauma mitigation, property protection, and the like may be benefited by liquids chosen to be attractive, or repulsive. Similarly, training, such as law enforcement training where the smell of gun powder, rancid or putrid smells, other uncomfortable or unfamiliar smells, or the like which may affect judgment, may be used to create more realistic environments for training.

Similarly, military training may benefit from soldiers trained in the presence of selected odors contributing to a more realistic environment. As one of the five senses, the sense of smell is particularly acute in many persons, and causes many sensations and reactions that are not ordinarily achievable in maneuvers. A realistic situation includes sight, sound, and smell for best training.

Similarly, livestock and poultry growers may use a system in accordance with the invention for air purification, disinfectant, or antimicrobial action, and the like.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 15 is a right end elevation view thereof;

FIG. 16 is a left end elevation view thereof;

FIG. 17 is a top plan view thereof;

FIG. 18 is a bottom plan view thereof; and

DETAILED DESCRIPTION OF THE PREFERRED EMBODIMENTS

Figure 1:
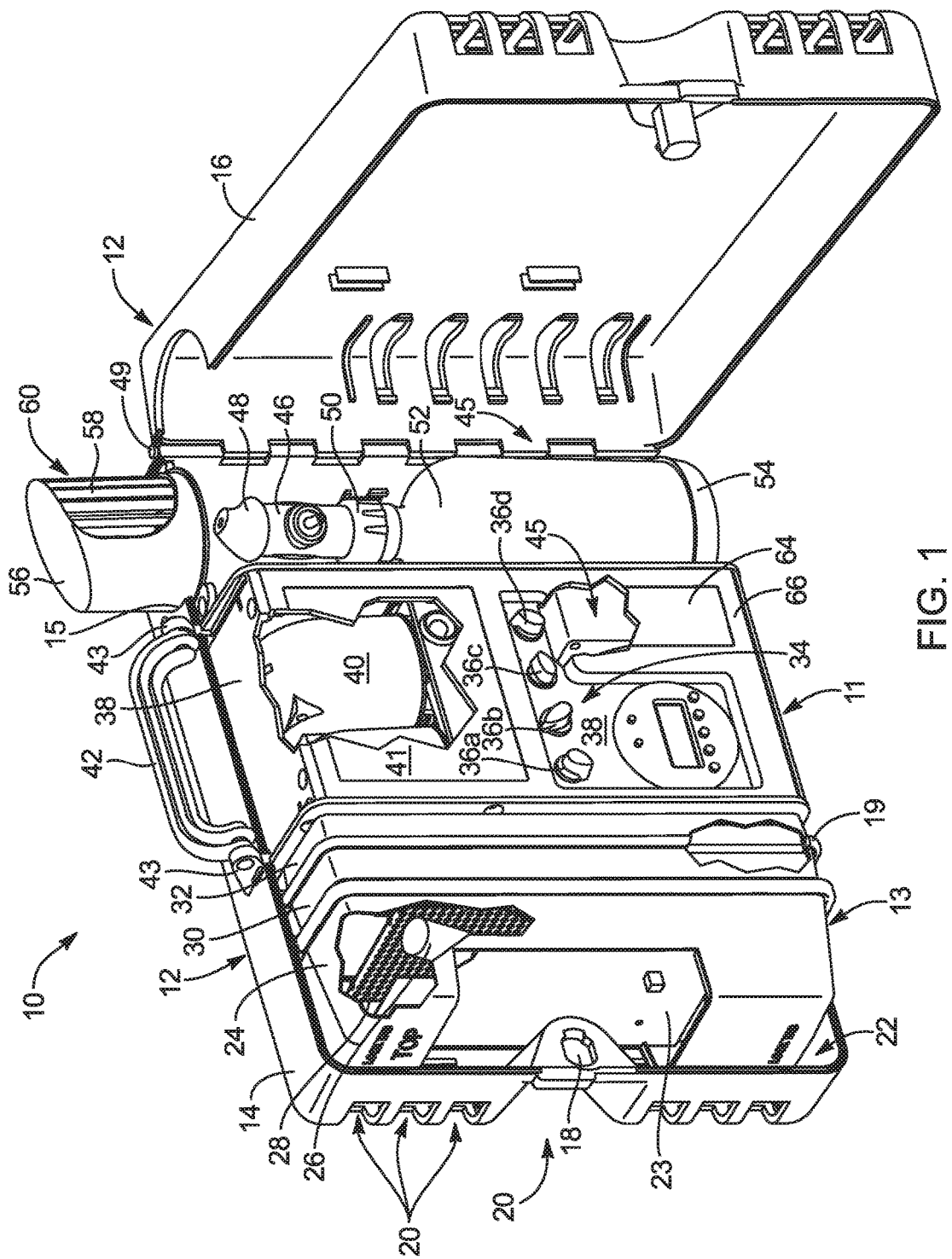
FIG. 1 is a front, top quarter, perspective view of an apparatus in accordance with the invention, showing the housing or case with the door or cover open.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIGS. 1-6, while referring generally to FIGS. 1-19, a system 10 in accordance with the invention may be manufactured as a modular system, susceptible to user maintenance and repair, onsite. Moreover, a system 10 in accordance with the invention provides not only aroma diffusion or diffusion of an operating liquid atomized to be introduced into an atmosphere of an enclosed space, but also purification of the air used to drive the system 10, and to atomize the liquid. As used herein, the liquid will typically be an oil, such as an essential oil used for aromatherapy, antibacterial treatment of a space, or the like. Such liquids may include oils, alcohols, other solvents, antimicrobials, and the like. Such liquids may also be combinations of various components, in order to obtain multiple benefits from a single liquid combination.

In the illustrated embodiment, the system 10 may be driven by an electrical module 11 that contains the powered components of the system 10. The entire system 10 may be enclosed in a housing 12 that includes a base 14 and door 16 that close together in a clamshell-like arrangement. For example, a germicidal module 13 may fit in the base 14, upstream from the electrical module 11. Meanwhile, downstream, through a collar 15, formed as a relief 15 or collar 15 in the base 14 and door 16, may be an exit port for treated air.

In the illustrated embodiment, a retainer 17 or clip 17 may be formed on the door 16, or on the base 14 to hold spare parts, replacement components, and the like. For example, a holder for filter media may be used. However, more difficult items to locate may be such items as tubes, which may wear, age, or the like. Thus, a retainer 17 or clip 17 in the case 12, or multiple retainers 17, may be used to provide readily-accessible components, that may need replacement over time.

A lock 18 may be useful for multiple reasons. For example, tampering with controls may be expensive, damaging to the system 10, damaging to the environment being treated by the system 10, or may be problematic, given the value of liquids that may be dispensed in the system 10. Thus, providing a lock 18 will assure that the base 14 and door 16 are locked together and inaccessible by unauthorized persons. In one embodiment a key on a retractable line system 191 is hidden from view in the well 70 of the base 14. Thus, a key is retracted into the well 70, not visible to a casual observer, yet accessible to an authorized, knowledgeable person servicing the system 10. Thus the lock 18 provides some protection against tampering, while the key retractor 191 provides a spring-loaded, retractable line holding a key ring with a key available. Such retractable line systems are often worn by maintenance personnel as a retractable key ring on a belt-connected assembly as known in the art.

Filtration may be done upon intake, but also through a filter module 19 positioned between the germicidal module 13, and the electrical module 11 downstream therefrom. In the illustrated embodiment, the passage of air is from an inlet 20 through a filter 22. Air passes then into the germicidal module 13, followed by the filter module 19, and the electrical module 11. The electrical module 11 is thereby cooled by the principal flow of air flowing through the system 10.

In the illustrated embodiment, the germicidal module 13 may include a baffle 23. The outer surface, or convex surface of the baffle 23 may serve as an air baffle to redirect air into the chamber 24. The chamber 24 or ultraviolet chamber 24 operates by a light source 26 emitting an ultraviolet light irradiation. Typically, the light source 26 will emit a strong ultraviolet wavelength of light that is reflected from the concave side of the baffle 23 as a reflector 23. That is, the baffle 23 may operate as a baffle 23 for air incoming from the inlet 20, but also on the opposite face thereof, operate as a reflector 23. Thus, a highly reflective material, such as a metal, may be disposed on the back or downstream face of the baffle 23.

Typically, the indirect light from the source, may thus be recycled, or recaptured, by the reflector 23. In one embodiment, a catalytic screen 28, such as a metal, or metallic-coated, screen may operate to ionize oxygen. Ionized oxygen may result in free oxygen ions, but will often result in creation of ozone, a combination of three atoms of oxygen, that is fundamentally unstable, and highly reactive. Thus, any microbe, such as a bacterium, virus, or the like, may be killed directly by ultraviolet radiation, may be damaged or killed by oxidation by an oxygen ion near the catalytic screen 28, or may be influenced by both. One kill mechanism is typically pure radiation from the light source 26, whether direct or reflective. Another is chemical damage to a cellular organism by oxygen ions. Oxygenation, or oxidation is effectively the same effect as burning. The temperature may not be as high, but the chemical result is that of oxidation or consuming. Accordingly, the reaction of chemicals within a microbe can destroy the cell.

Figure 2:
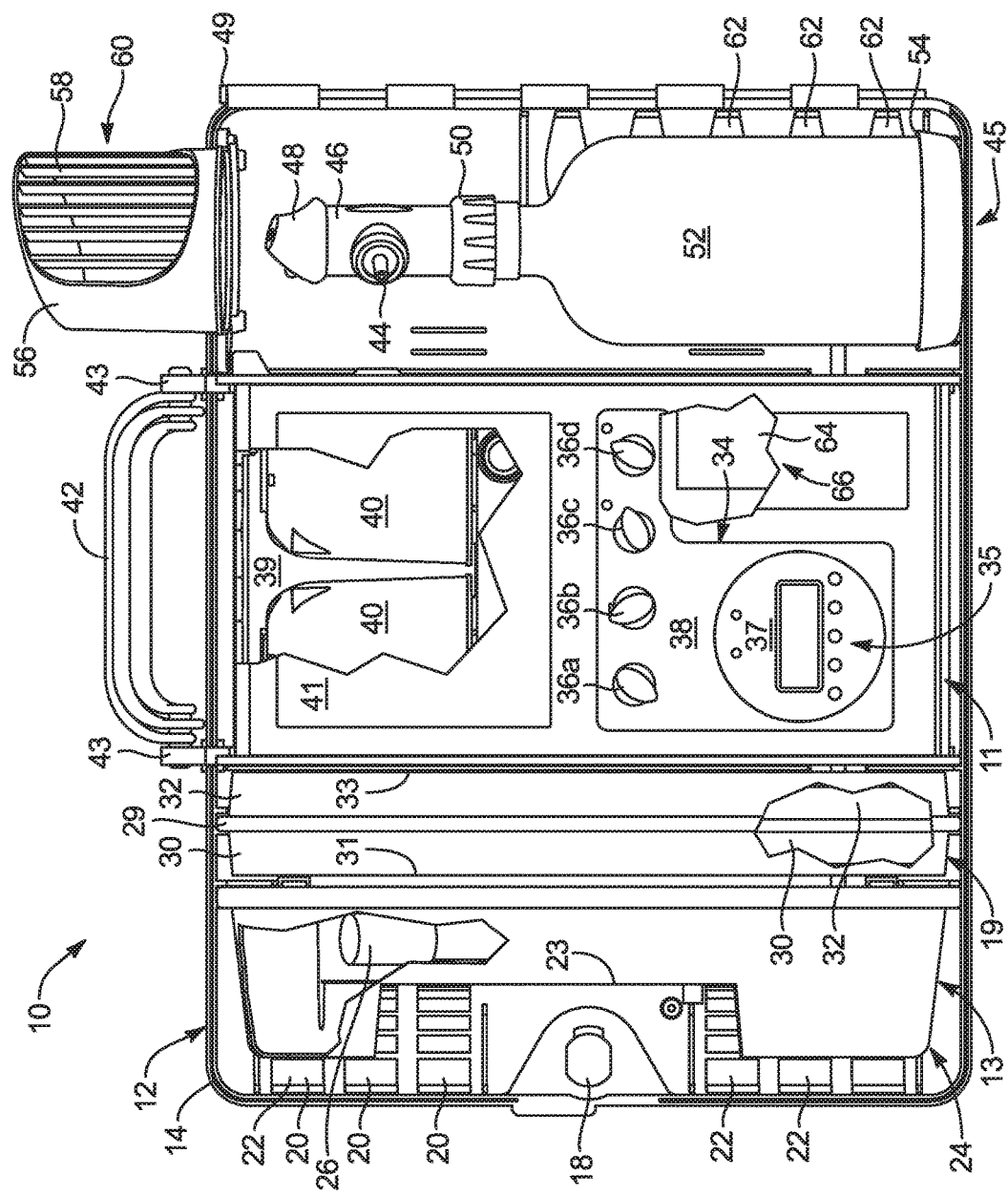
FIG. 2 is a front elevation view of the system, in the base portion of the case, absent the cover.
Figure 3:
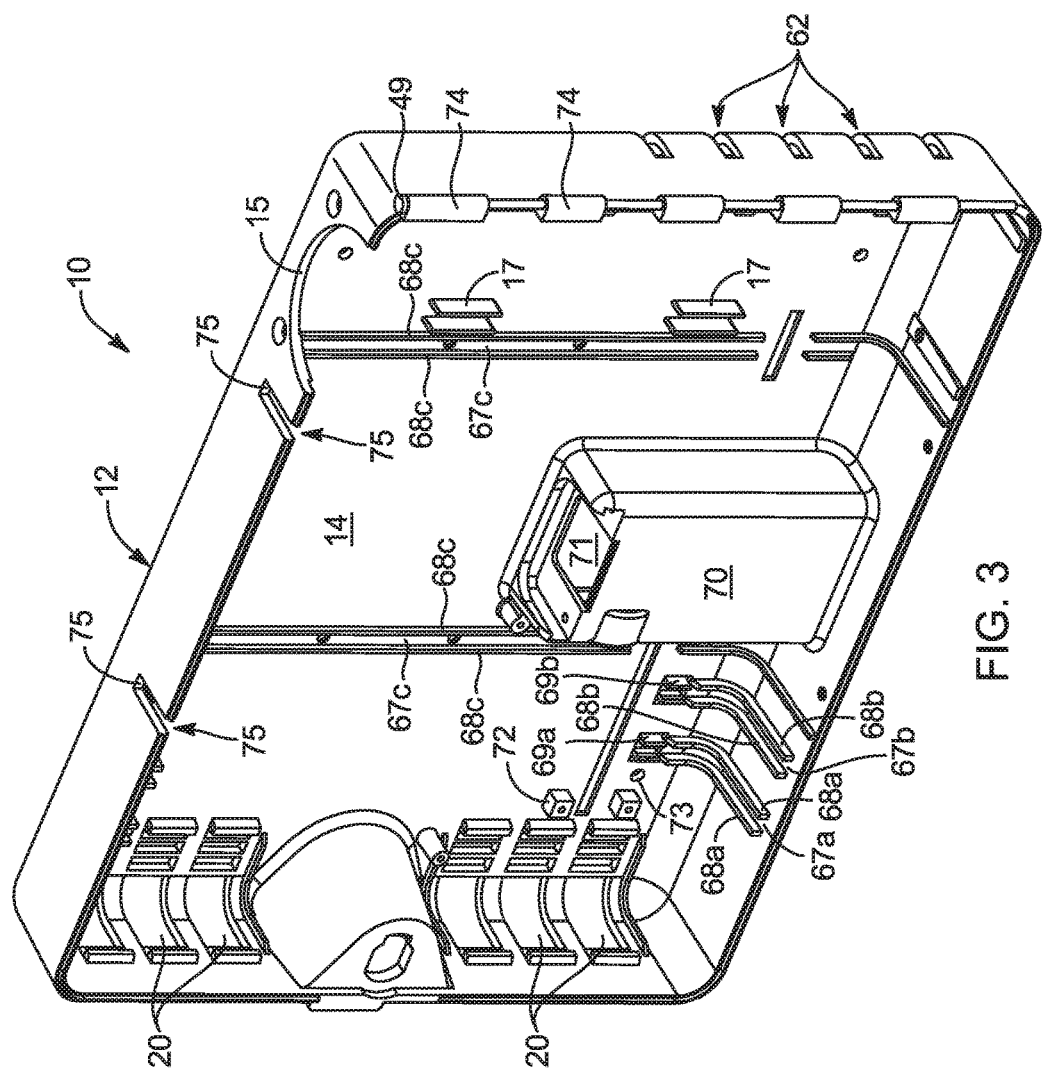
FIG. 3 is a front perspective view of the base portion of the housing for a system in accordance with the invention.
Figure 4:
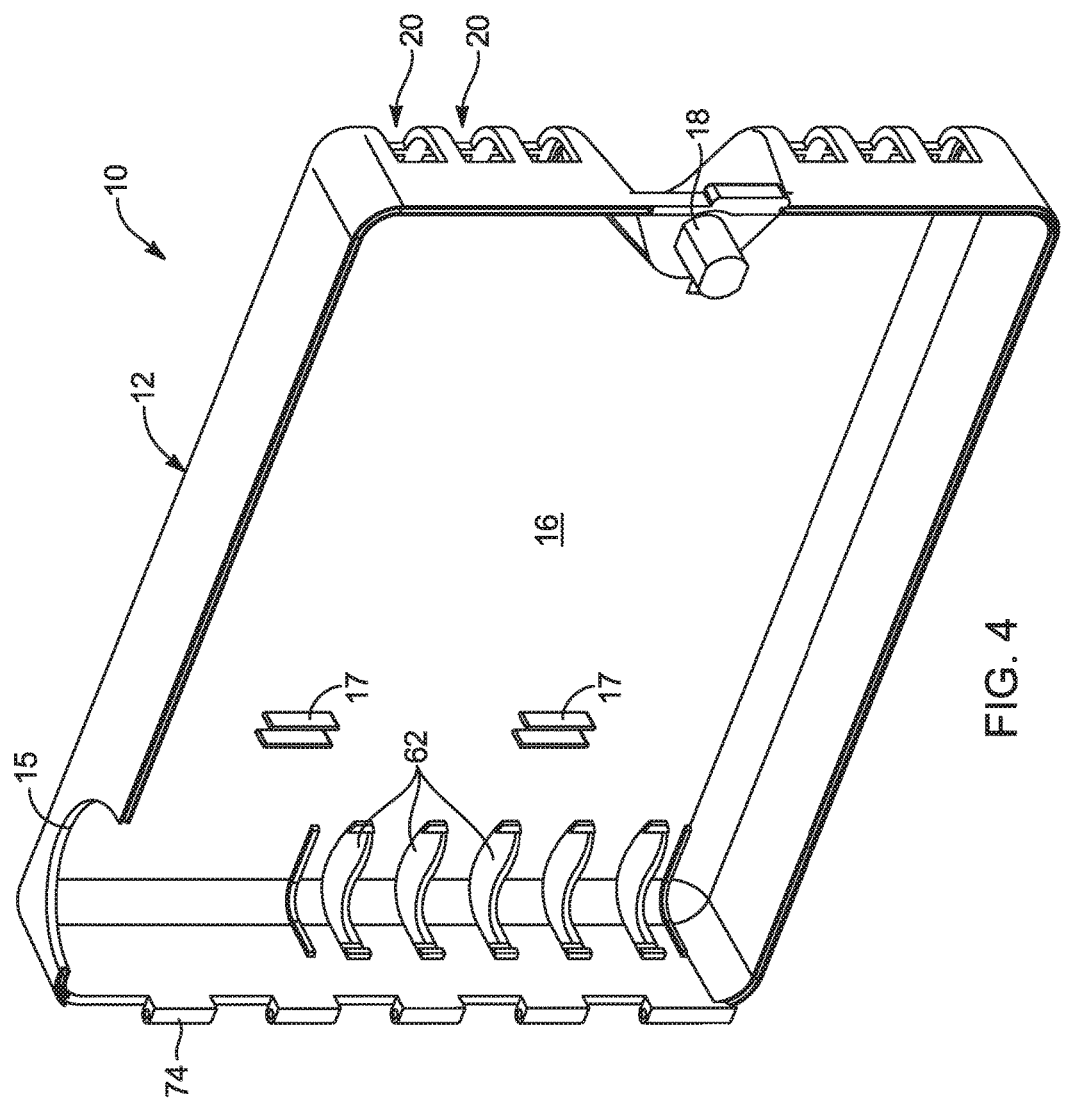
FIG. 4 is a rear perspective view of the inside of the cover.

Referring to FIGS. 1-2, while referring generally to FIGS. 1-19, a system 10 in accordance with the invention may include one or more filters in a filter module 19. For example, in the illustrated embodiment, two sides of the filter module 19 are combined on a slide 29 or center portion 29. The slide 29 operates as a frame 29 holding a filter 30 upstream, captured behind a grill 31, and a second filter 32 downstream, captured by a grill 33. In the illustrated embodiment, the filter 30 may have a mesh size smaller than the incoming filter 22, but larger than that of the third level filter 32 downstream.

In the illustrated embodiment, various combinations of filters 22, 30, 32 may be used. In certain embodiments, the grills 31, 33 may operate as frames, engaging the slide 29. The grills 31, 33 may be glued as a unitary system to the slide 29, all three being formed of similar or compatible plastics. They may be solvent or adhesive bonded to one another. In other embodiments, brackets on the slide 29 may receive the grills 31, 33 sliding thereinto, to form a unitary filtration module 19.

In certain embodiments, fibers treated with capture materials that will hold items that stay on impact may be suitable. In some embodiments, a mat, bat, fiber, fabric, or the like may be used for the second filter 32 in the filter module 19. For example, a folded paper filter, a folded screen, a folded glass fiber mesh, non woven fabric, or the like may be used. In any suitable embodiment, the power used to drive air or draw air through the filtration module 19 should be matched with the drag, caused by porosity or the size and number of apertures in the filters 30, 32. One must be aware that the system 10 will adjust to match the power requirements for airflow with the airflow and the filtration capacity. In certain embodiments, the filtration may be sub-micron in at least one of the filters 30, 32. In other embodiments, the filtration may be done to sub micron sizes by a tortuous path, that does not have an affirmatively smaller aperture, but rather simply attaches and holds such particles.

A control system 34 may be contained within the electrical module 11. For example, in the illustrated embodiment, various control buttons 35 may provide operational controls such as set up.

For example, in the illustrated embodiment, a set of control buttons 35 may provide set up of the system, with information displayed on a display 37 in which the control buttons 35 are integrated. Meanwhile, placed thereabove, is a set of knobs 36 or controller knobs 36 that control the operation of the fan, the output volumetric flow of liquid from the diffuser, the delay time between operation in a less than a 100 percent duty cycle, and the total run time in each individual cycle of the overall duty cycle.

Meanwhile, the buttons 35 associated with the display 37 may control for example, a computer program selection. It may scroll through various programmatic operational schemes. A selection button for setting or confirming a particular setting, opening up settings for operation, closing settings as acceptable or confirmed, and the like may also be included.

Meanwhile, incremental buttons may be included for incrementing week, hour, minute, seconds, or the like on a clock for program timing. Meanwhile, a decrement button may be included for decrementing weeks, hours, minutes, or seconds of time. Meanwhile, there may be available a button for erasing or backing over a previous selection, and the like. Typically, a reset key to return to a default position, or to return to a known location in the process of programming may be available as well. In certain embodiments, various on and off switches as well as programming and operating indicators may be included.

The control system 34 may be installed effectively behind or against the back of a recessed portion 38 of the electrical module 11. In the illustrated embodiment, the various control knobs 36a, 36b, 36c, 36d, are used to control, respectively, the fan speed, the pump pressure and effective output, the rest time or wait time, sometimes referred to as dead time or delay time, in which the system is not operating, and the run time duration of operation after a rest time, respectively. Thus, the overall passage of air, the amount of atomized or diffused liquid, the down time, and the run duration, may all be controlled directly by the controller knobs 36. It should be noted herein that all reference numerals refer to specific items. Trailing letters following reference numerals refer to specific instances of the item identified by the reference numeral. Thus, the control knobs 36a, 36b, 36c, 36d correspond to specific instances of control knobs 36 generally. It is proper to refer the number alone to mean any or all, and to the number with the reference letter to identify a specific instance.

A pump housing 39 or pump housing portion 39 of the electrical module 11 may house one or more pumps 40. These pumps may be as described in the patents incorporated hereinabove by reference. In certain embodiments, the system 10 may operate with a single pump 40. In other embodiments, two pumps 40 may be operated in parallel to feed compressed air to the diffuser 46 of diffused liquid.

Considering the overall structure of the electrical module 11, a front panel 41 may actually include a pump housing portion 39 defining the space in which the pumps 40 will reside, as well as a control portion 38 or recessed portion 38 that will hold the control system 34, with its control buttons 35 and knobs 36. Likewise, the display 37 is positioned in the recess portion 38. In the illustrated embodiment, a fan housing 66 or fan housing portion 66 may fill out the remainder of the front panel 41. More will be discussed about the various constituent components in addition to the panel 41 of the electrical module 11.

The handle 42 is secured by brackets 43 to the electrical module 11. For example, the electrical module 11 contains two or more motors. The controllers also contain electrical components. Electrical components constitute weight. Thus, additional strength, modularity, and support are engineered into the electrical module 11. The handle 42 secured by brackets 43 to the module 11, may lift the entire system 10. It may lift the electrical module 11 out, once securements are removed that hold the electrical module 11 inside the base 14 of the housing 12.

The pumps 40 provide compressed air, purified through the germicidal module 13 and filter module 19, typically as that principal flow of air passes through the electrical module 11, cooling the electrical components therein. Thus, the fan 64 in the fan housing 66 or fan housing region 66, draws and drives the principal airflow. Nevertheless, a portion of the airflow is drawn off from the principal airflow to the one or more pumps 40 to pressurize a flow of air in a line 44 feeding the diffusion module 45.

The diffusion module 45, may be thought of as the arrangement of components, or the housed region including all the components. Thus, in the illustrated embodiment, the pressure line 44 feeds directly into a diffuser 46 or atomizer 46. This atomizer 46 has been discussed in detail in the patents incorporated herein by reference. The atomizer 46 feeds a flow of atomized liquid droplets out through a nozzle 48.

At the opposite end from the nozzle 48, the diffuser 46 connects by way of an adapter 50 to a reservoir 52. The reservoir 52 is supported by a seat 54 formed into, or attached to the housing 12. In the illustrated embodiment, the seat 54 is secured to the base portion 14 of the housing 12. It may be supported by, or may be in contact with, the bottom or floor of the door 16 of the housing 12 in certain embodiments.

The diffuser module 45 receives the principal flow of air passed from the electrical module 11 into the diffusion module 45. Thus, the principal flow of air, after warming itself by cooling the electrical module 11, is passed through the space of the diffuser module 45. The flow of air past the nozzle 48 acts as an eductor drawing with itself, by a transfer of momentum thereto, the flow of compressed air. Entrained therein are the ultra-small-diameter liquid droplets from the nozzle 48 as generated in the diffuser 46.

Various separation schemes, discussed in the patents incorporated herein by reference, as well as elsewhere in this disclosure, identify the operation of the diffuser 46 and the nozzle 48. Obtaining a comparatively very small droplet size of liquid droplets is hereby defined as obtaining a size thereof entrained into the flow of air out of the nozzle 48, and into the shroud 56 such that droplets persist for from about one to about 30 minutes in ambient air without settling out. Thus, the entire flow, including the portion drawn off by the pumps 40 into the line 44, is recombined by eduction to enter the shroud 56.

That director 56 provides an exit 60 or outlet 60 from the system 10. In the illustrated embodiment, the shroud 56 may be rotated with respect to the collar 15 in the housing 12 to provide directionality. Moreover, a grill 58 or louvers 58 may be formed at the outlet 60 to provide vanes to direct flow exiting the system 10 through the outlet 60 of the shroud 56.

Practically, the germicidal capability of the system 10 is served in at least two ways by the shroud 56 or director 56. The volumetric flow rate provided by a fan 64 is selected to provide an exit velocity through the outlet 60 that will project into the enclosed spaced serviced by the system 10. By maintaining a suitable volumetric flow rate (cubic feet per minute, cubic meters per second, or the like), the system 10 may project an entrainment jet from the exit 60, directed by the orientation of the housing 56 or shroud 56, and the louvers 58. Typically, twenty outlet diameters of distance may still include or demonstrate velocity of the jet or plume being projected from the outlet 60.

For example, near the outlet 60, the jet or plume of air, laden with liquid droplets travels at a substantially faster velocity than surrounding air, which is substantially still. According to the rules of Newtonian momentum transfer, and the equations thereof, well understood fluid mechanics, the jet will exchange momentum with the surrounding air, slowing the outer perimeter of the jet, and speeding up the engaged portion of the surrounding air. With additional distance away from the outlet 60, the jet will expand in size, decrease in maximum velocity, and spread out its velocity distribution in space.

The plume will occupy more area, have less speed, and involve more volume and mass of air. Thus, the diffuser 46 diffuses into the principal flow by an eduction scheme with the nozzle 48 inside the housing 12. The educted flow of scented air passes out of the shroud 56, through the outlet 60, and continues to entrain ambient air in a jet extending many diameters away from the outlet 60. This may be actual diameter, and may be characterized in equations using effective diameter.

Effective diameter in fluid mechanics is referred to as a hydraulic diameter. A hydraulic diameter is four times the area available for passage of a fluid divided by the wetted perimeter, or the overall perimeter to which the passing fluid is exposed.

The diffuser module 45 may include, or operate cooperatively with windows 62 or sight glasses 62. For example, the sight windows 62 or sight glasses 62 may include flexible, closed windows fitted into the corners of the housing 12 to prevent the free flow of air in or out through the windows 62. Meanwhile, the windows 62 provide a sight glass 62 for observation of the liquid level in the reservoir 52. The sight glasses 62 or windows 62 may be spaced at approximately one quarter, one half, three quarters, and full height, with respect to the shoulder of the reservoir 52. More or fewer of these sight windows 62 may be formed in the housing 12 as desired.

A fan 64 in the fan housing 66 may be of a suitable form, whether a squirrel-cage, centrifugal, screw, or rotary impeller type. It has been found that a rotary screw impeller, such as a pancake fan 64 serves adequately with minimum electrical power draw.

A hinge pin 49 may connect the base 12 to the cover 14. In the illustrated embodiment, an ejector pin 49 serves this function well by providing a head that would normally function as the ejection portion itself, and the push rod acting as the hinge pin 49. By proper sizing and a suitable core pull, the ejector pin 49 serves as a hinge pin 49.

Referring to FIGS. 3-4, while continuing to refer generally to FIGS. 1-19, the housing 12 of the system 10 may include a back portion or base 14. A front portion or cover 16 operates as a door 16 opening the housing 12 to expose the modules 11, 13, 19, 45 therewithin. In the illustrated embodiment, the components have been removed to show the structure of the housing 12.

One may note that the apertures 20 or inlets 20 to which first stage filters 22 are fitted, occupy corners of the housing 12. Likewise, the lock 18 requires a shape that causes an incursion into the interior of the housing 12. Nevertheless, the shape of the germicidal module 13 accommodates the relief required to receive the lock 18.

A series of slots 67 includes slots 67*a*, 67*b*, 67*c*, and may include others. The slots 67 receive the individual components. For example, the slot 67*a* receives the germicidal module 13, fitting around an outer rim of the housing thereof. The slots 67 are formed by rails 68 or guides 68. In the illustrated embodiment, the edges of the respective components 11, 13, 19, 45 may be formed to be received by the slots 67, as constrained by the rails 68 or guides 68. Thus, the rails 68 or guides 68 in combination with their respective modules 11, 13, 19, 45 form somewhat of a seal urging all of the principal airflow to pass therethrough.

A detent 69 corresponding to certain slots 67 may provide capture of a module 13, 19. Thus, in certain embodiments, the modules 11, 13, 19 may be hand insertable, retained, and removable, all without tools. An undercut in each of the detents 69a, 69b may be matched by a swell or expansion in the dimensions of an outer rim of a module 11, 13, 19, thus providing for ready insertion, snap to lock, and snap to unlock and remove.

A well 70 may encroach on the inner volume of the base 14. In the illustrated embodiment, the well 70 provides an external well 70 that can receive a power supply, plugs, other power connection devices, and the like. Thus, the system 10 may be totally integrated to connect to a power source by a suitable means, including a transformer or other power supply, without affecting the outer envelope, that is the outer volume or the outer volumetric maxima, of the system 10. Mounted against a wall, for example, the base 14 can contain in the well 70 a power supply or plugs to a wall or line power source.

The well 70 may be provided with an aperture 71 for passing cables, as necessary, through from outside the housing 12 inside to the controller system 34, pumps 40, and fans 64 in the electrical module 11 of the system 10.

Various bosses 72 may be formed, of any suitable length, as needed, such as for receiving fasteners. Relieved regions 73 may represent surfaces flush with the outer surface of the housing 12, but recesses that pass almost through those outer surfaces. The relieved regions 73 may provide a comparatively thinner wall in the housing 12 in order to readily receive a fastener penetrating therethrough.

For example, a user can punch the point of a screw through the relieve region 73, due to the very thin wall. On the other hand, spurious sources or leaks of air may not spring up through unused holes or other apertures in the walls of the housing 12. Thus, a variety of relieve regions 73 may be provided through which a user or installer can puncture, typically the hand, a screw or other sharp pointed fastener.

Hinge lugs 74 may be formed in each of the base 14 and door 16 portions of the housing 12. In one innovative design of a housing 12 in accordance with the invention, the hinge lugs 74 are sized to match a diameter of an ejection pin 49 from an injection molding machine. Meanwhile, the drive shaft for driving an ejector pin 49 may have a diameter selected to be the diameter of a hole formed by a core pull through the hinge lugs 74. Thus, total alignment of the hinge lugs 74, may be formed by a core pull element that is removed before the mold is opened. Thus, assembly may be done by sliding a new ejector pin 49 down, as a hinge pin 49, through each of the hinge lugs 74, to make a piano-hinge type of attachment of the door 16 to the housing 12.

Slots 75 may be formed to receive the brackets 43 of the handle 42. Thus, the electrical module 11 may be released by removing fasteners, and may be picked up and taken out of the base 14, directly, without removal of or from the handle 42. For example, in the illustrated embodiment, the brackets 43 are integrally and homogeneously formed with the framing structure of the electrical module 11. They capture the handle 42 during assembly. Thus, the handle 42 is integrated with the electrical module 11, which may then be integrated with the overall housing 12, and other modules 13, 19, 45.

In the illustrated embodiment, the rails 68c may capture and seal a portion of the electrical module 11 securely to the base 14 of the housing 12. The rails 68c operate as guides about the slots 67c formed by the rail sets 68c. Each receives a matching edge of a portion of the electrical module 11. Various apertures and fasteners (e.g. screws) may secure the electrical module 11 into the case 12 or housing 12.

Typically, the weights of the germicidal module 13 and filter module 19 typically weighing ounces, are such that the detents 69 exert sufficient force to maintain them in place. In contrast, the electrical module 11 may weigh several pounds owing to the motors, magnets, wire, and the like contained therein. Accordingly, it is normally safer to have the electrical module 11 firmly maintained within the slots 67 by fasteners through the walls of the housing 12, rather than simply by detents 69.

Figure 5:
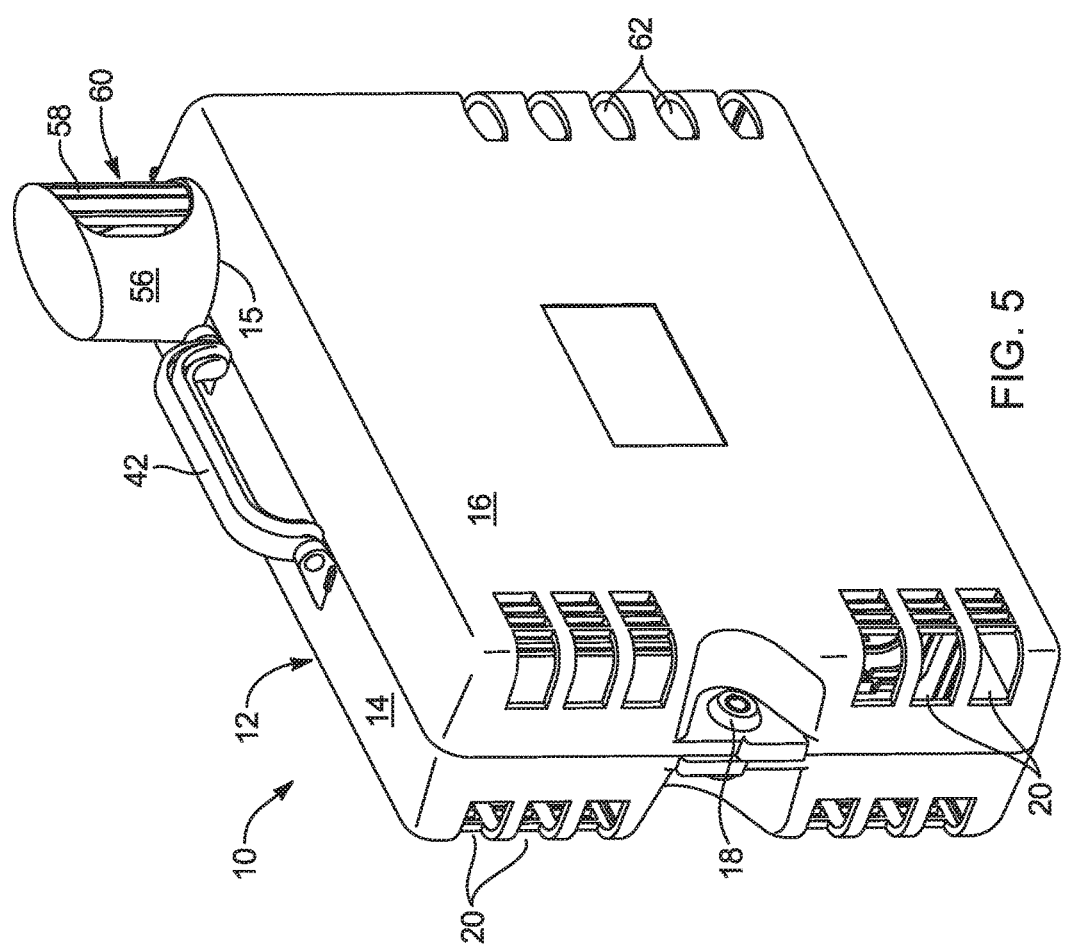
FIG. 5 is a front, top quarter, perspective view of a system in accordance with the invention, in a closed and operable configuration.
Figure 6:
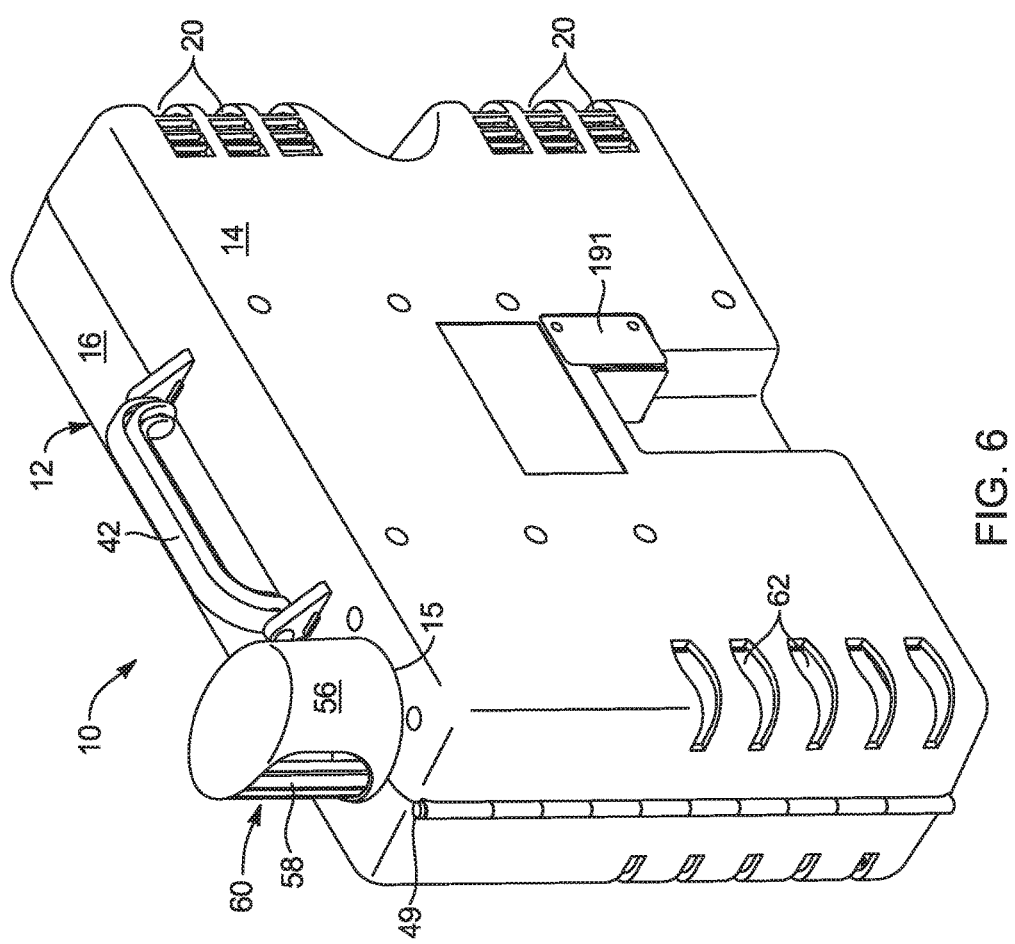
FIG. 6 is a top, rear quarter, perspective view thereof.

Referring to FIGS. 5-6, while continuing to refer generally to FIGS. 1-19, a system 10 encased in a housing 12 may be carried by a handle 42 for temporary duty. For example, a chambermaid, homeowner, or traveler may carry the system 10 by handle 42 from room to room for use. Feet secured to the bottom of the housing 12 may support the system 10 on a surface, such as a desk, cabinet, counter, or the like in order to treat a room.

A homeowner, a chambermaid, or the like may carry the system 10 by the handle 42 into a room, activate it by powering it up from wall current, operating it according to the control system 34, for a temporary time period. The effect may be one of providing a scenting of the enclosed area, fumigation, extermination of microbes or bugs, or any combination. In other embodiments, apertures in the base 14 may receive fasteners to secure the system 10 to a wall.

Meanwhile, from the exterior, the sight glass windows 62 may be used to determine the condition of the reservoir 52, and its content level. The lock 18 may be accessed for opening and closing the housing 12. Typically, the shroud 56 rotates in the collar 15, which may include a keeper securing to the housing 12 a rim or flange of the shroud 56. This maintains position, yet provides for rotary motion with respect to the housing 12. Thus, the louvers 58 at the outlet 60 may be aimed in any suitable direction.

Figure 7:
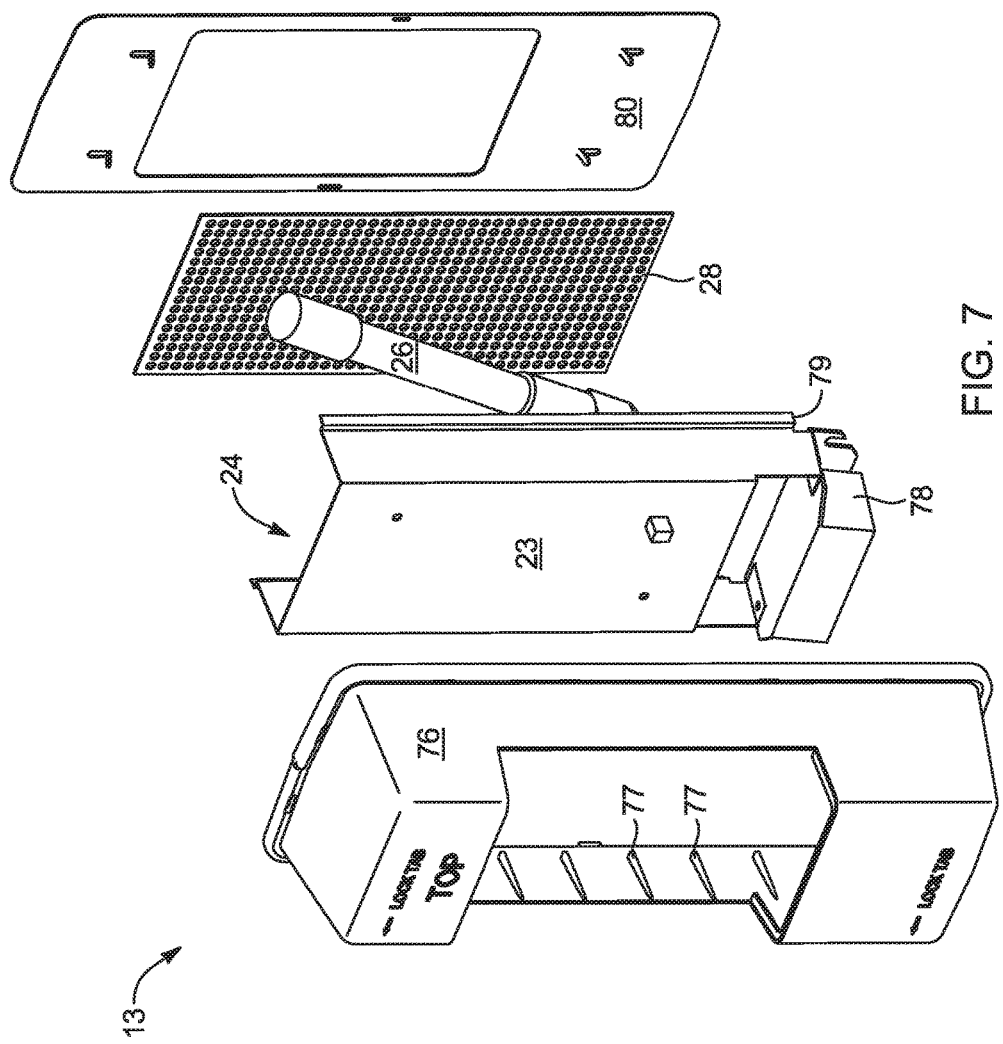
FIG. 7 is an exploded, perspective view of a germicidal module from the system of FIGS. 1-6.

Referring to FIG. 7, while continuing to refer generally to FIGS. 1-19, the germicidal module 13 may include a box 76 or housing 76 that operates as a frame 76 to contain the remaining components thereof. In the illustrated embodiment, for example, a baffle 23 defines a light chamber 24 served by a reflector 23 on the concave side of the baffle 23 formed on the convex side of the barrier 23. Typically, as illustrated, a ballast 78 may operate in conjunction with a light source 26 in the light chamber 24. Typically, the light band is in the ultraviolet region in order to provide the best, direct germicidal effect.

The catalytic screen 28 and the reflector 23 may include catalytic metals to provide for catalysis of oxygen atoms from ambient air as charged, ionic particles. Light irradiation in the ultraviolet bandwidth of the light source 26 may provide direct killing of microbes, such as bacteria and viruses. The catalysis of oxygen into oxygen ions at the metallic screen 28 provides oxygen ions, ozone, or both to react chemically with the cells of microbes and viruses, thereby destroying them.

The keeper 80 is secured, and may be shaped to support or register the catalytic screen 28 thereon, holding the catalytic stream 28 against edges of the baffle 23 or reflector 23. The entire assembly may be secured by the keeper 80 within the rim or edge of the housing 76 of the germicidal module 13. Securement may be by glue, fasteners, clips, screws, or the like.

The registers 77 space the baffle 23 or reflector 23 properly to clamp or otherwise hold the catalytic screen 28 between a rail 79 or edge 79 of the baffle element 23 and the keeper 80. The registers 77 thus fit against the edge 79 or rail 79 providing a reaction force for the clamping by the keeper 80. The keeper 80 is provided with an aperture sized to expose the majority of the catalytic screen 28 to the passage of air through the aperture and out of the germicidal module 13.

In certain embodiments, the germicidal module 13 may have a rim sized to snap into a detent 69, at the end of traverse or sliding along a slot 67. Thus, for example, a slot 67*a* may receive a rim of a housing 76, which may then be snapped into a detent 69*a* once in the proper position. Thus, the germicidal module 13 may be removed for service, replacement, repair, or the like. No tools are required.

In addition to viruses, bacteria, and the like, the germicidal module 13 is also responsive to kill plant matter, such as mold spores, and the like. In general, the photo catalytic oxidation process will oxidize anything that is reactive, which includes substantially all living single-cell matter and the like. The chemical reaction with oxygen effectively destroys by oxidation, which is the same chemical effect observed in rust, burning, or the like.

Figure 8:
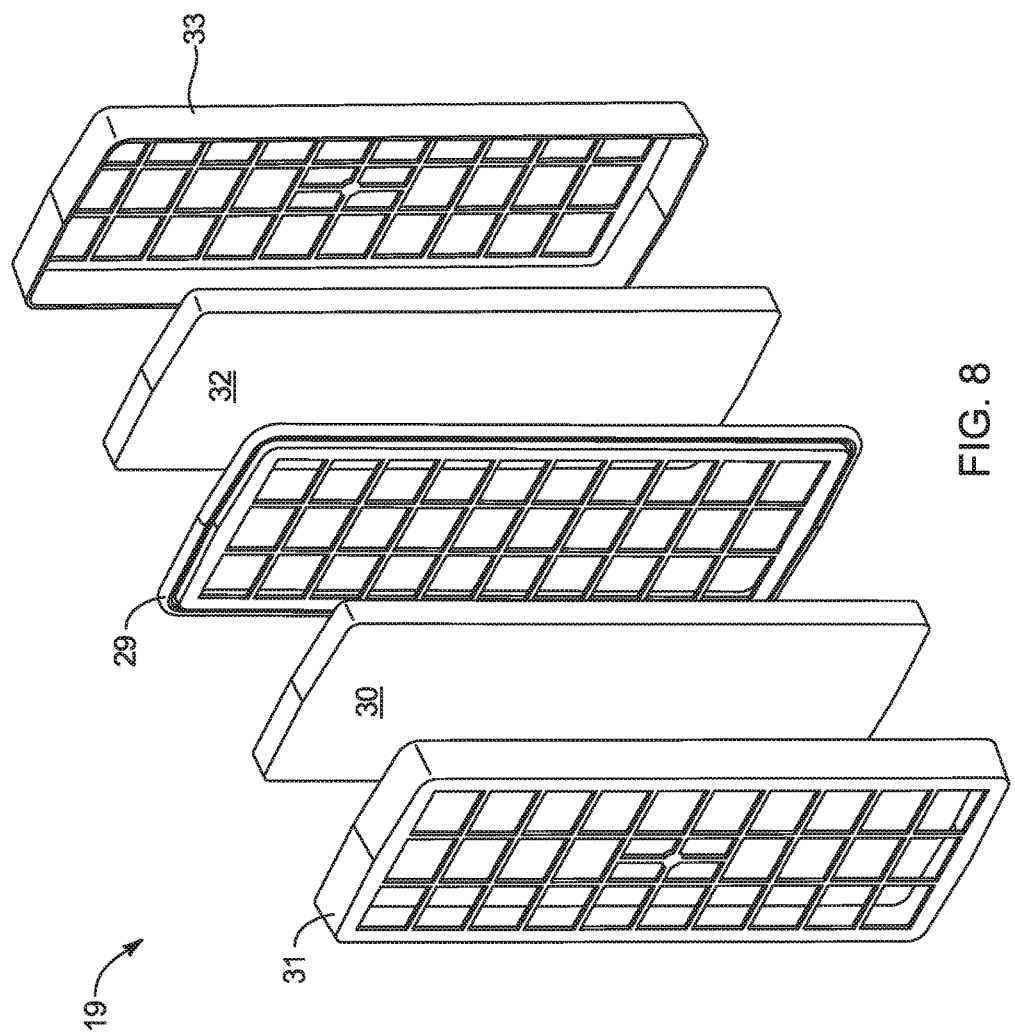
FIG. 8 is an exploded, perspective view of one embodiment of a filtration module of the system of FIGS. 1-6.

Referring to FIG. 8, the filter module 19 may include a slide 29 fitted to a slot 67 and capable of securement by a detent 69. Thus, a grill 31 may secure a first filter medium 30 against the grill of the slide 29. The slide 29 may be thought of as the backbone, or base 29 of the filter module 19. On the opposite side of the slide 29, a second, usually different, filter medium 32 may be secured by another grill 33. The grills 31, 33 may be glued to the slide 29. In other embodiments, the grills 31, 33 may be secured by sliding, snapping, clipping, or other fastening mechanisms to the slide 29.

In the illustrated embodiment, the slide 29 includes a rim that is offset, such that the grill thereof is closer to the grill 31 of the first filter medium 30, and an additional space is provided to receive the other, second, filter medium 32. Thus, the grills 31, 33 may actually be the same size, even identical, and yet a filter medium 30, 32 need not be the same size. Thus, an offset of the grill in the slide 29 may provide additional space for filter medium 32. In this way, folded media may operate as the second filter medium 32.

Figure 9:
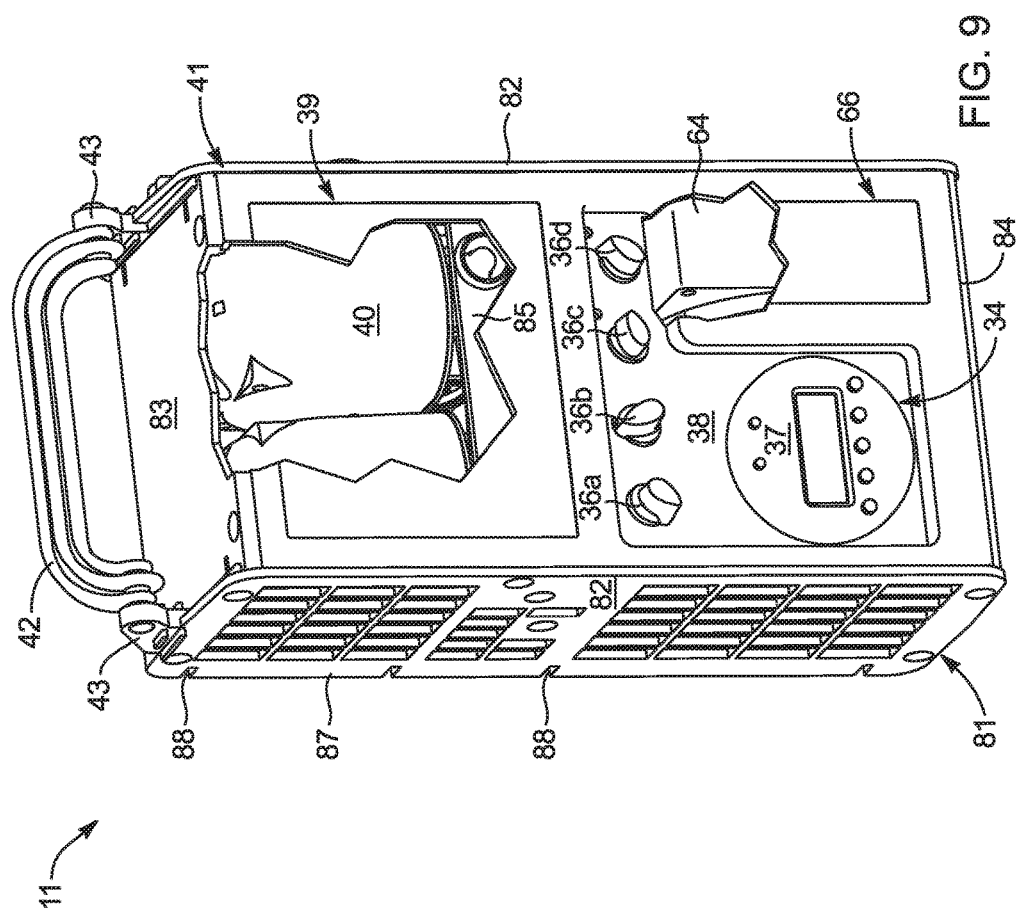
FIG. 9 is a front perspective view, partially cut away for visibility, of the electrical module of the system of FIGS. 1-6.

Referring to FIG. 9, the electrical module 11 is illustrated in isolation from the overall system 10. In the illustrated embodiment, as discussed hereinabove, the handle 42 is inherent or organic to the electrical module 11. Brackets 43 may be secured to, and even molded homogenously with the appropriate portions of the frame 81.

The frame 81 represents the structural elements of the electrical module 11. For example, in the illustrated embodiment, the frame 81 or cage 81 may include sides 82 or side panels 82. These may be mirror images of one another. A top panel 83 may secure to the side panels 82, thus forming a more-or-less rectangular structure.

In the illustrated embodiment, the brackets 43 are molded homogenously with, from the same material at the same time, the side panels 82. A bottom panel 84 may secure to each of the side panels 82, at the bottom ends thereof. A support 85 or sled 85 may support one or more pumps 40. The support 85 or sled 85 may ride on slides 86 or rails 86 formed in each of the side panels 82. In this way, the entire pump assembly constituted by the pumps 40 on their sled 85 may be withdrawn, serviced, and replaced in the frame 81, by an individual user.

As a practical matter, the edges 87 of the side panels 82 may fit into the slots 67*c* between the rails 68*c* in the base 14 of the housing 12. Rather than circular apertures, such as blind holes for receiving screws, slots 88 may be formed in each of the panels 82, 83, 84 to receive fasteners. By using self-tapping screws, for example, adequate strength may be obtained, and each of the panels 82, 83, 84 may be manufactured by a simple two-piece mold, with no core pulls required.

In selected embodiments, a slide 29 may be configured to have a reduced height on one side. Thus, the slide 29 may slide into a fixture, or slot 88 in the base 14 of the housing 12. Moreover, in certain embodiments, the slide 29 itself is not planar symmetrical along the axis of flow, or distribution of the components, of FIG. 8. For example, as illustrated, the grill portion of the slide 29 is toward the left side, but an extension exists on the right side. Accordingly, a larger cavity is created between the slide 29, and the grill 33 than is formed between the slide 29 and the grill 31. For example, in folded medium 32, such as paper, folded fiberglass, or glass mats, additional axis space may be required.

Accordingly, the cavity formed between the slide 29 and the grill 33 may be larger than that of the cavity between the slide 29 and the grill 31. Thus, the filter medium 32 may be thicker by any preselected amount than the filter medium 30. In the illustrated embodiment, for example, the grill of the slide 29 actually extends into the outer framing toward the grill 31. In contrast, the grill 33 is spaced away therefrom and may house a larger thickness of filter medium 32.

Figure 10:
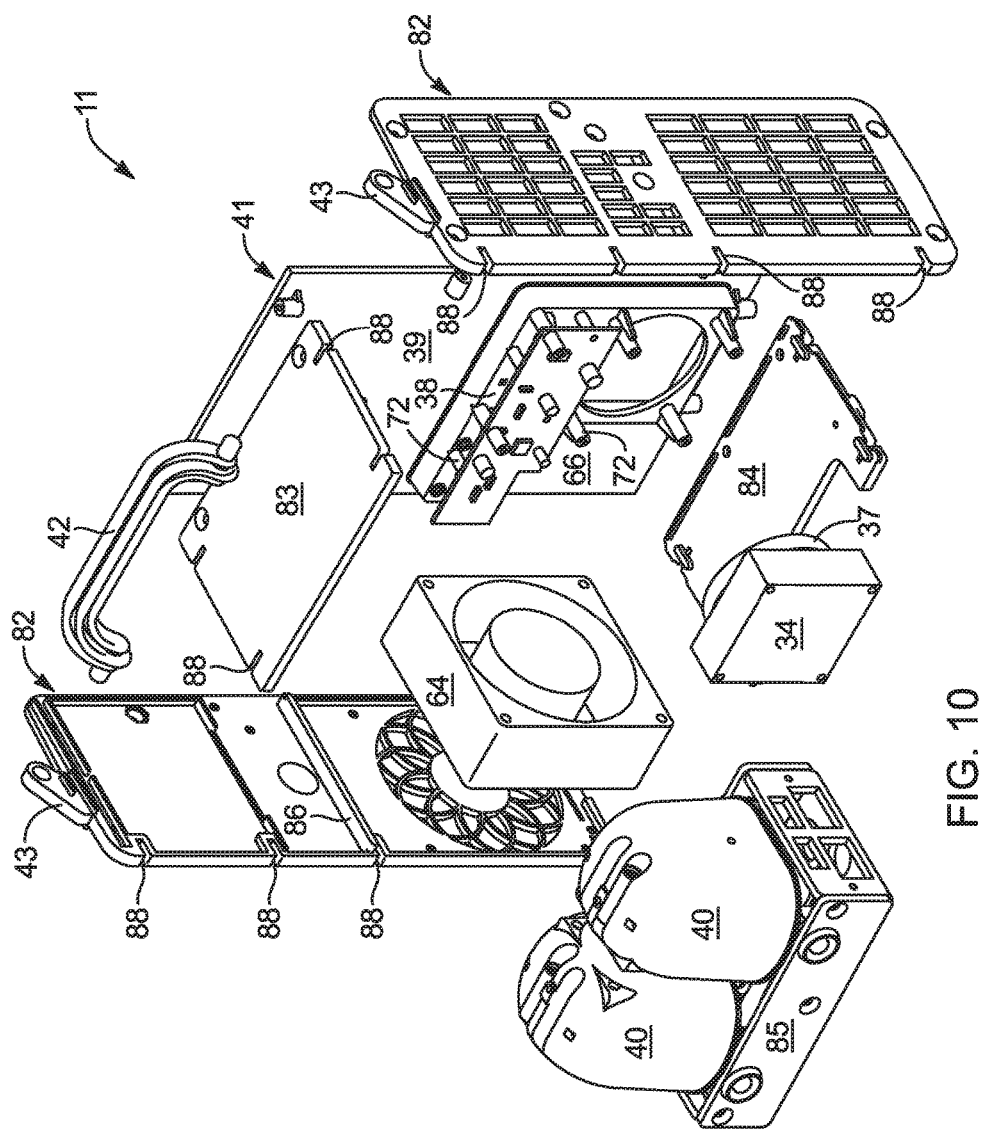
FIG. 10 is a rear, exploded, perspective view of the electrical module of FIG. 9.
Figure 11:
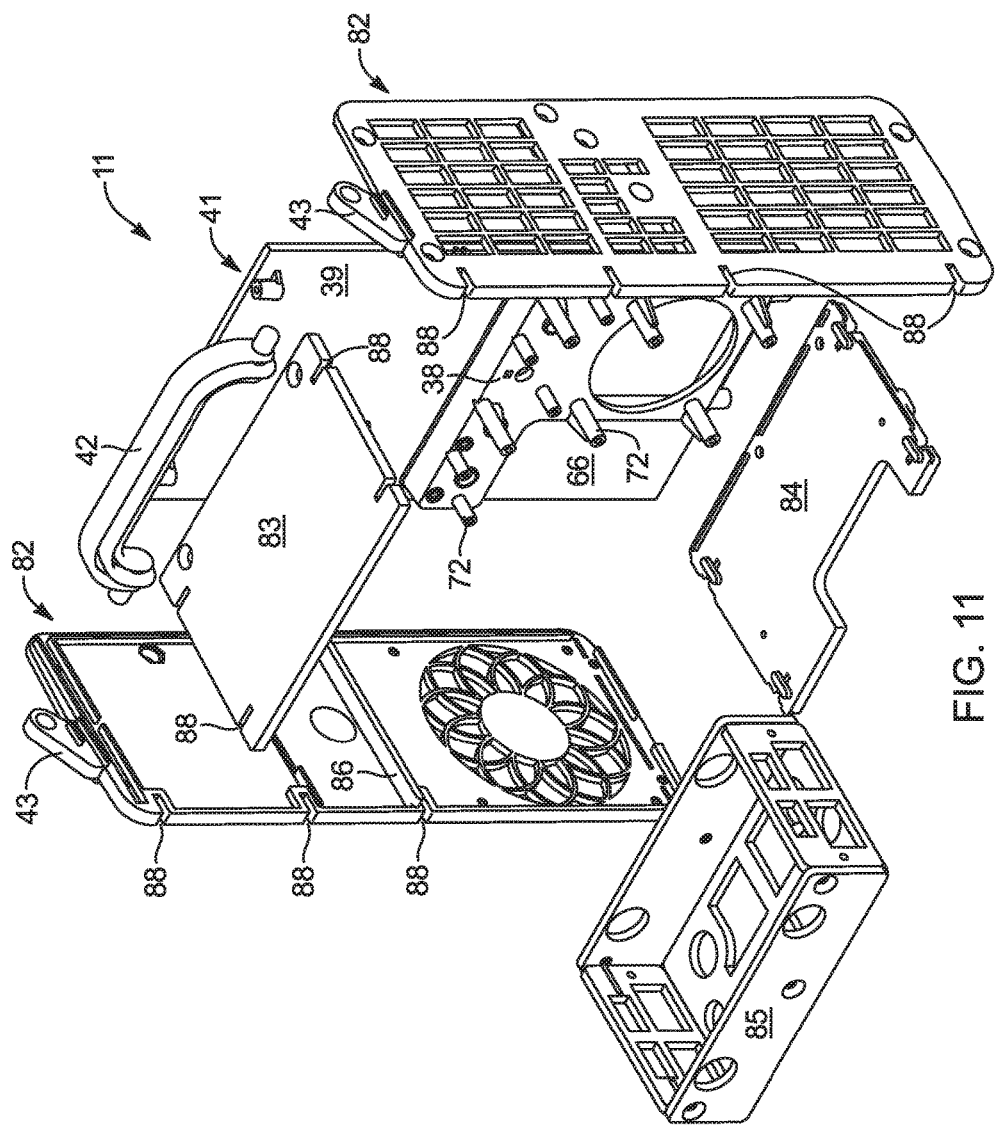
FIG. 11 is a rear, perspective, exploded view of the frame of the electrical module of FIGS. 9 and 10.

Referring to FIGS. 9-11, while continuing to refer generally to FIGS. 1-19, the electrical module 11 may be secured together by fasteners, such as screws, rivets, or the like. Typically, screws embedded through apertures in the various panels 82, 83, 84, may be received into slots 88 in adjacent panels 82, 83, 84, for securing the frame 81 together. Typically, the components, such as a control system 34, display 37, pumps 40, and fans 64 may be secured to their respective panels 82, 83, 84 by suitable fasteners in blind holes, slots, or the like.

However, threading a screw type fastener into a side of a flat or comparatively flat object is not a problem. Such cavities may be molded with suitable draft in a two-piece injection mold or other molding system. Thus, the end- or edge-oriented fasteners, which must penetrate the slots 88, would otherwise require core pulls. This effort may be avoided in the illustrated, manufactured product.

Referring to FIGS. 10-11, while continuing to refer generally to FIGS. 1-19, the electrical module 11 is illustrated in exploded view showing details of each of the components therein. For example, the fan 64 operates secured to one side panel. The knobs 36 of the controller 34, and the display 37, all on the front side thereof, fit through apertures in the front panel 41.

The various bosses 72 may be formed, to the extent needed, at any suitable length. They may have blind holes formed therein for receiving self-tapping screws or other fasteners, such as rivets. Thus, the securement of the various panels 82, 83, 84 may be complete, to one another and the securement of the components 34, 40, 64 thereto may also be effected.

Typically, the fan 64 will be protected by an open material in the corresponding side panel 82. A large and open grill system may be formed where appropriate to encourage cooling air flow through the electrical module 11 and over all of the components therein. Meanwhile, the rails 86 may be formed in the side panels 82 to receive the sled 85 supporting the pumps 40.

Figure 12:
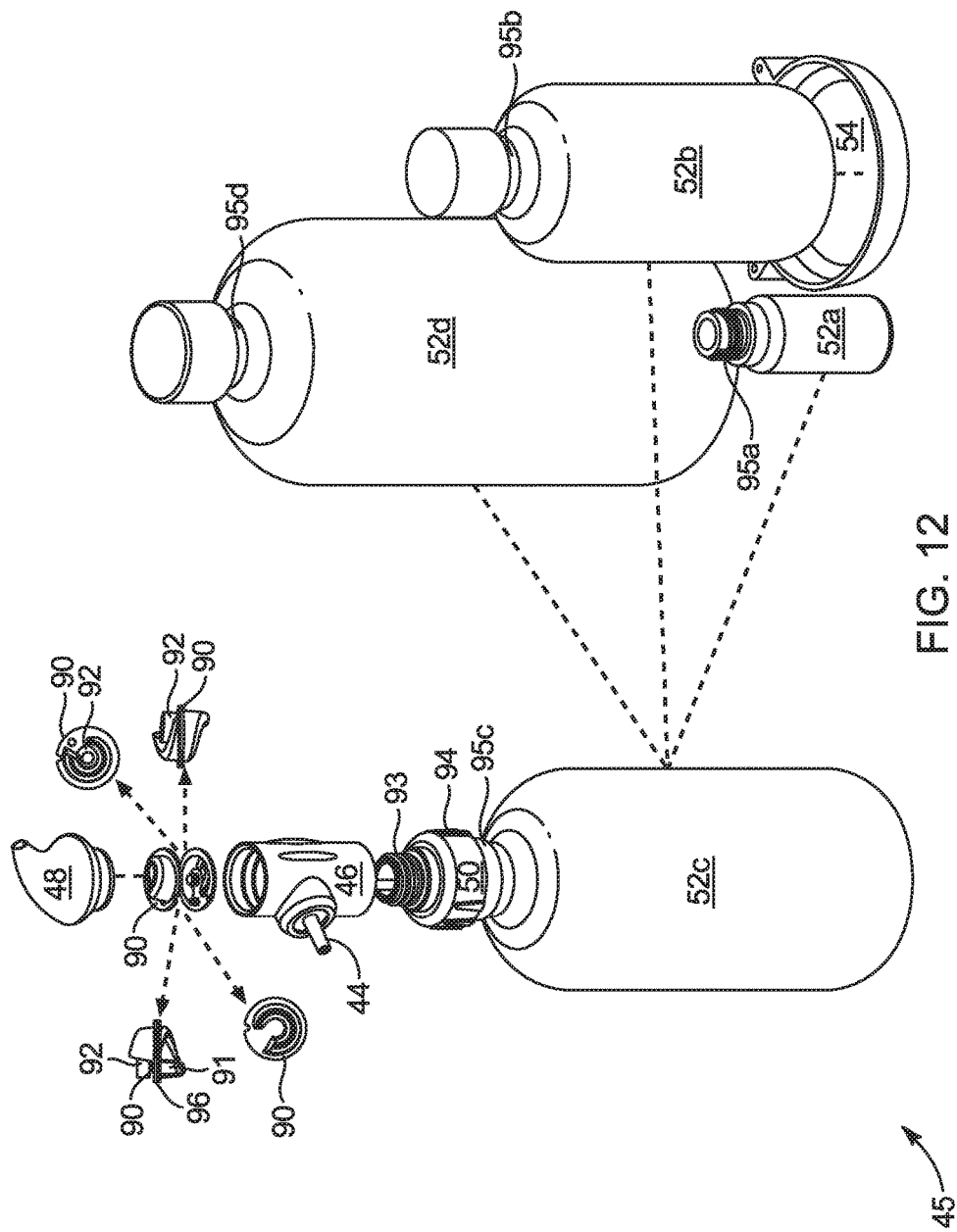
FIG. 12 is an exploded, perspective view of the components of the diffuser module in the system of FIGS. 1-19.
Figure 13:
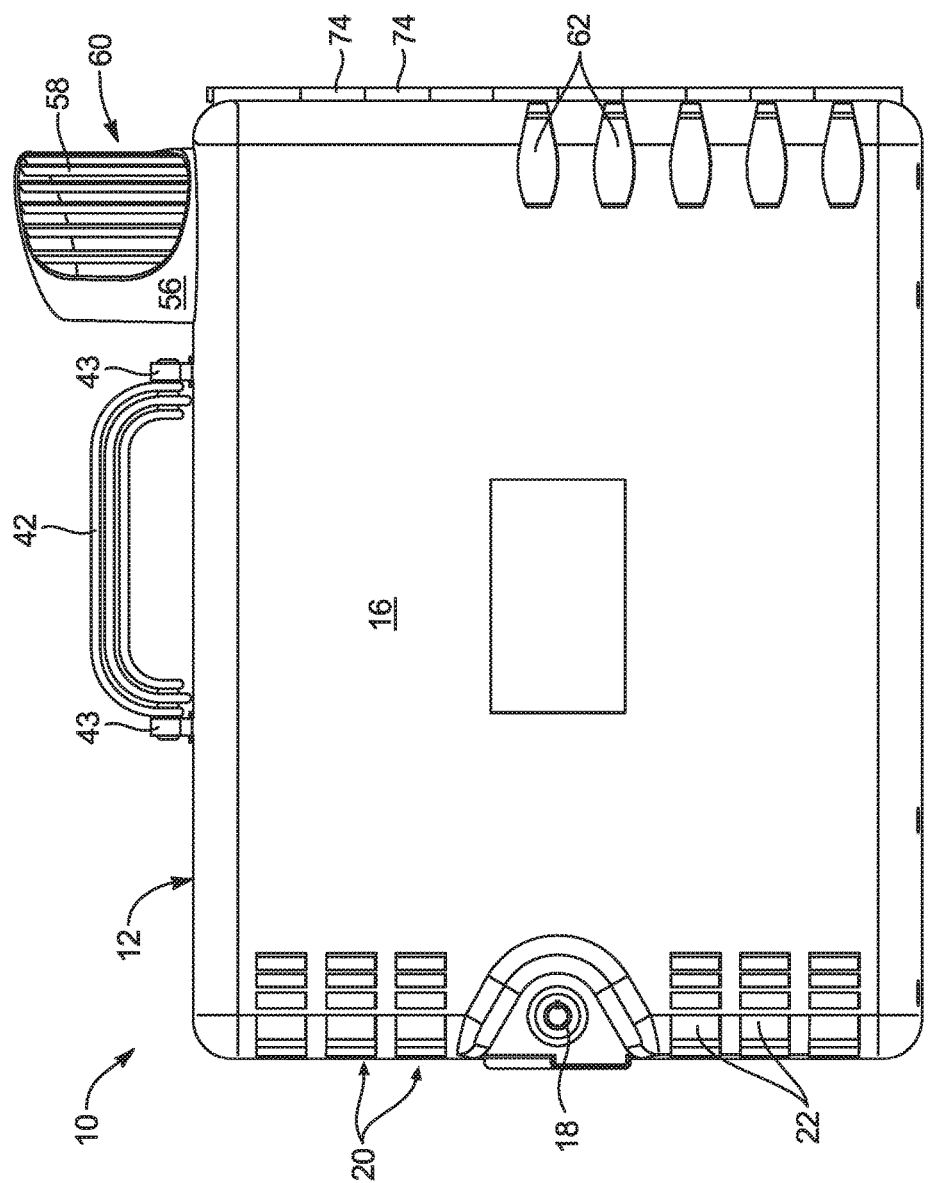
FIG. 13 is a front elevation view of the system of FIGS. 1-19.
Figure 14:
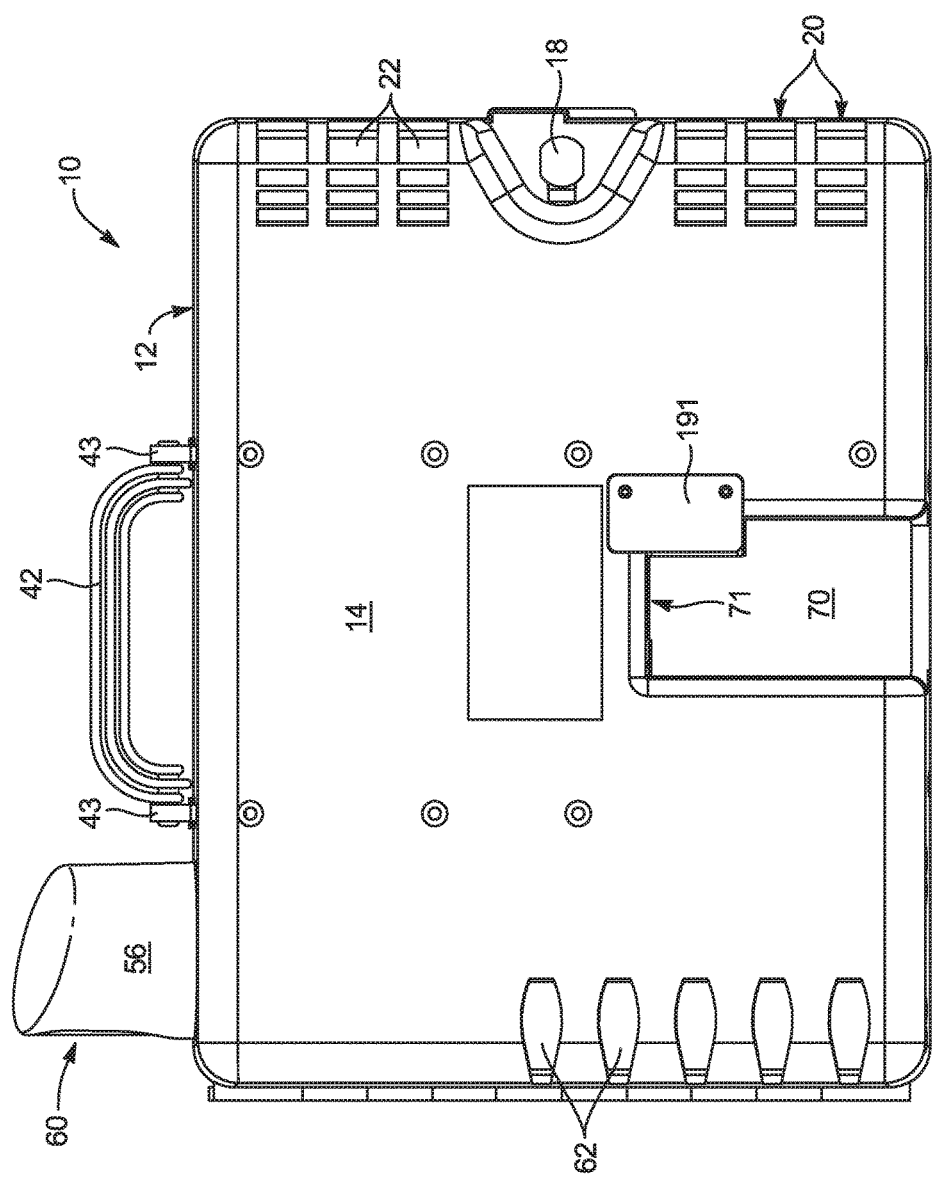
FIG. 14 is a rear elevation view thereof.

Referring to FIG. 12, while continuing to refer generally to FIGS. 1-19, the diffuser module 45 includes several components, including a choice of reservoirs 52. Again, trailing reference letters refer to specific instances of the item identified by the reference number. Thus, it is proper to speak of any or all of the reservoirs 52, or of each individual reservoir 52a, 52b, 52c, 52d as appropriate.

In the illustrated embodiment, the diffuser module 45 may include or be incorporated within a region of the housing 12 that houses all the components illustrated in FIG. 12. In one embodiment, a diffuser 46 may be provided with an adapter 50. The adapter 50 may include a fixture 93 or fitting 93 adapted to fit with, within, or without (outside) the diffuser 46.

A line 44 or tube 44 is shown for carrying liquid from the reservoir 52 up through the line and into the diffuser 46. Similarly, the fitting 93 fits or is adapted to connect, such as by threads, bayonet fitting, slot, compression fitting, or the like with the diffuser 46.

Likewise, the adapter 50 also includes a fitting 94 configured to fit with a specific type of fitting 95 of a reservoir 52. In the illustrated embodiment, various sizes of reservoirs 52a, 52b, 52c, 52d are illustrated. The system 10, and the diffuser module 45, in particular, will accommodate any of the reservoirs 52 illustrated and more. Other shapes and sizes may also be used.

This is contrast to typical systems. Conventionally, canisters or cartridges contain liquids to be atomized. The diffuser 46, or whatever mechanism was used as an atomizer 46 is typically built into the cap or top portion of the cartridge-type reservoir 52. As a result, customer selection of reservoir type, size, content, and operating system 10 using such reservoir for delivery for atomized liquids, has been limited, constricted, and rendered much more expensive.

Sufficient expense is involved that most atomization systems for industrial applications are not even sold. They are typically owned and maintained by a supplier of the canister or cartridge style reservoir 52. In the illustrated embodiment, a supply of adapters 50 can fit any common reservoir type 52. For example, one ounce, two ounce, eight ounce, sixteen ounce, and thirty two ounce bottles of essential oils are available. Similarly, other bottle styles and sizes, made of various materials, whether glass or polymer, are also available.

The adapters 50 in accordance with the invention adapt between the diffuser 46, and any suitable reservoir 52 requested by a customer. Therefore, the adapter 50 provides for a universal diffuser module 45, adaptable virtually to any source of liquids. Moreover, a user may simply select a particular type of reservoir 52, use an adapter 50 suitable for that reservoir 52, and then refill or re-purchase a generic reservoir 52 for use in the system 10.

The atomizer 46 may be fitted with a micro-cyclone 90. The micro-cyclone 90 or cyclone 90 contains a spiral channel 91. The channel 91 begins below a central plane 96, which is actually defined by a plate 96 formed thereby. In one embodiment, the micro-cyclone 90 is cast in a two-piece mold, as a comparatively thin walled casting. Vacuum forming may even operate to make such devices in certain embodiments.

As a vacuum formed or injection-molded part, the micro-cyclone 90 may be formed in two halves, each having a base plate 96 or plane 96 on which half the spiraling channel 91 or spiral-shaped channel 91 is formed. By remaining connected, at one small area or region, the two halves of the micro-cyclone 90 may be folded together, and snapped closed. For example, an aperture in one half, and a button or extension in the other half provide a detent to tie down the two halves together. Thus, held on one side by a continuation of the flange 96 or plate 96, the micro-cyclone 90 folds in half to double up. It snaps together to form the central plate 96, with a channel 91 spiraling from fully below the plate 96 to fully above it.

The entire cross-sectional area of the channel 91 may remain constant throughout the entire spiraling circular route, from below the plate 96 to above the plate 96. In the illustrated embodiment, it has been found appropriate and best functioning to keep the size of the channel 91 at constant area, and cross-section. Some atomized liquid particles, passing out through the channel 91 from the atomizer 46, pass into the channel 91, and out the nozzle 48.

Any larger particles, or the comparatively larger particles in the stream of air, tend to smash and coalesce against the inside of the outer wall of the channel 91. They drip back into the atomizer 46, or diffuser 46, to be re-atomized. Thus, only the comparatively smallest range of droplets is passed out to the nozzle 48. This provides higher efficiency, more effectiveness, and eliminates collection of oil droplets on surfaces outside the system 10.

In certain embodiment, the micro-cyclone 90 may include a dam 92 that begins at the innermost radius of the upper opening of the channel 91. It then passes in spiraling, circular, arcuate shape around to the upper outside wall of the channel 91. Eventually its lower edge rides up along that wall to the pre-selected height of the dam 92. The dam 92 typically ends at a gap just before the wall of the channel 91 at which it begins, at its innermost diameter. The gap provides for the retrieval or return of any oil that collects within the dam 92.

The dam 92 performs three significant functions. From its position in the micro-cyclone 90, the dam 92 collects liquid, makes a constructive gap, and changes direction of the flow. The dam 92 serves to fit close (from 10 to 50 mils, usually a bout 20) to a corresponding dam within the nozzle 48. Thus, the air must pass through a slot between the dam 92, and a corresponding dam extending down within the nozzle 48. Thus, an additional sharp change in direction tends to collect out overly large particles that are not small enough to remain entrained substantially with the air at any velocity within the system 10.

The dam 92 also serves as a noise barrier. In fact, the micro-cyclone 90, itself, by extending around an angle or included angle of about 330 degrees (typically from about 250 to about 380, and most preferably less than 360 degrees of included angle, with a target at about 330 degrees) provides a barrier to the passage of internal noise. Thus, the diffuser 46 operates extremely quietly compared to conventional diffusers.

In the illustrated embodiment, views of the micro-cyclone 90, moving in a clockwise direction, beginning in the upper right corner, show a top plan view, a right side elevation view, a bottom plan view, and a left side elevation view. In the center, the micro-cyclone 90 is shown in its two halves, separated. In reality, the two halves are never separated by that distance, since they are hinged together at one edge, and snapped together at an opposite edge of the plane 96 or plate 96.

In the illustrated embodiment, the bottle 52 or other type of reservoir 52 may be fitted to a seat 54 for support. The seat 54 may be formed in or may be secured to the housing 12, such as by securement to the base 14. Padding, by way of expandable, elastomeric, polymeric foam pads may be provided to stabilize a reservoir 52 with respect to the housing 12, the seat 54, or both. Thus, by adding or subtracting pads, or simply compressing pads, various sizes of reservoirs 52 may be fitted into the diffuser module 45.

The aperture, with the attachment penetrating therethrough, is visible in the small circle in the upper right hand corner of the top plan view. In the bottom plan view, the stud fit into the aperture is on the opposite side of the plane 96 or flange 96 thereof. Meanwhile, the noise suppression capability of the micro-cyclone 90 comes partly as a matter of the circuitous route, through the channel 91 and beyond. The plate 96 or flange 96 blocks the propagation of sound waves directly out of the barrel or central cavity of the diffuser 46. Similarly, by maintaining constant effective lengths, cross-section, and diameter, whistling is reduced in the channel 91. By diameter is meant the effective diameter. The cross-sectional area, long and short dimensions, shape, which tends to be a rounded rectangular shape and so forth, are maintained substantially constantly throughout the entire circular spiral rise of the channel 91 in the micro-cyclone 90.

Referring to FIGS. 13-18, the design of the apparatus 10 is viewed from a front elevation, rear elevation, right end elevation, left end elevation, top plan, and bottom plan view. In the illustrated embodiment, various apertures 98, 99 may be provided. For example, certain apertures 98 may be formed to provide a location for extending fasteners through the wall of the housing 12 in order to secure selected components of the various modules 11, 13, 19, 45 within the housing 12. Other apertures 99 are formed to receive feet that will support the housing 12 and the system 10 on a surface.

Figure 19:
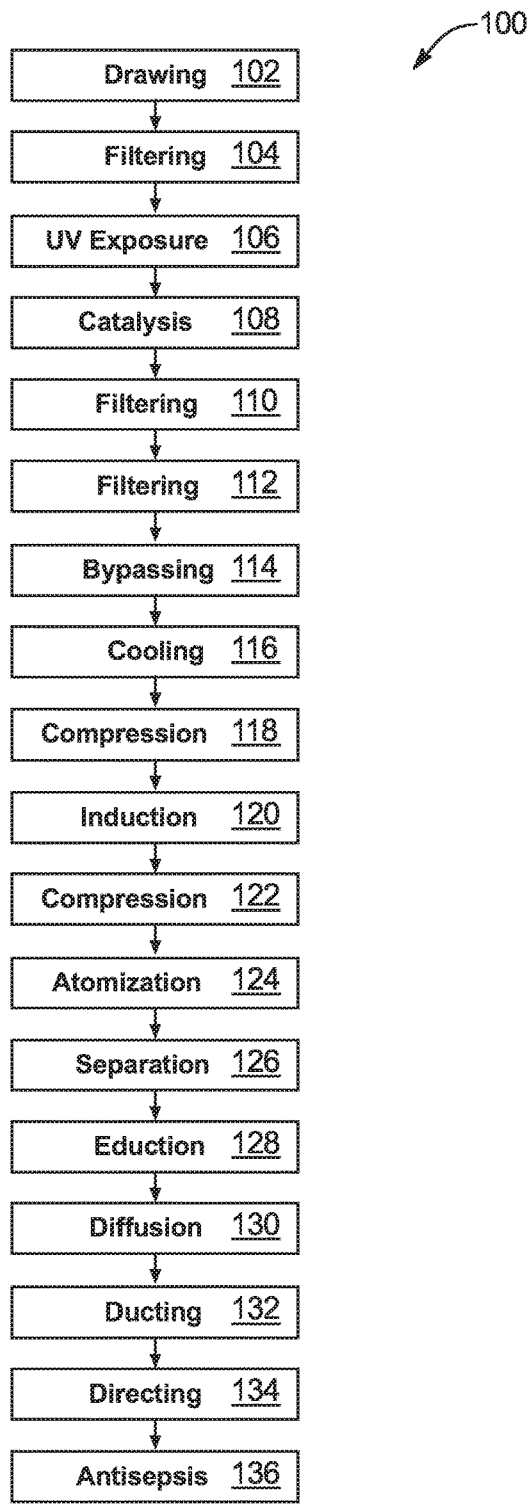
FIG. 19 is a schematic block diagram of one embodiment of a process in accordance with the invention.

Referring to FIG. 19, a process 100 in accordance with the invention may begin outside the system 10 by drawing 102 a quantity or flow volume of ambient air from a treated, enclosed, habitable space. Typically, upon drawing 102 a quantity of air through the inlet 20, filtering 104 is completed at a highest (e.g. largest, grossest) size consideration by filters 22 or filter media 22 positioned in the inlet 20. Typically, foam filter media backed by keepers, may be deformed into the corner shape of the housing 12 in order to fit snuggly within the inlets 20.

Following this outermost, largest-particle-size filtering 104, exposure 106 to a germicidal module 13 may occur. Exposure 106 may include exposure to ultraviolet light, ozone, oxygen ions, or the like. In the illustrated embodiment, exposure 106 may include all three. That is, ultraviolet light provides a direct kill of microbes, while catalytic screens 28 may provide ionization of oxygen for the formation of oxygen radicals and ozone to react with and kill microbes. Catalysis 108 may occur on the reflector 23 or baffle 23 of the germicidal module 13, but will typically occur in about the catalytic screen 28 as a result of the ultraviolet light or ultraviolet irradiation.

Filtering 110 by a filter medium 30 is second in the overall flow of the principal flow through the system 10. It may be followed by filtering 112 through an additional, typically more restrictive, filter medium 32. Bypassing 114 may include drawing the majority of the principal flow coming through the inlets 20 and filter module 19 into the electrical module 11.

Meanwhile, a flow of air passing into pumps 40 is drawn from the principal flow, and pressurized to flow into a line 44 driving a diffuser 46. Thus, bypassing 114 is substantially supporting the cooling 116 of the components within the electrical module 11. For example, the actual majority of airflow typically bypasses the diffuser 46. It first passes into the electrical module 11, cooling 116 the principal electrical components, such as the fan 64, pump 40 or pumps 40, and the control system 34 with its associated electronics. It then flows around the outside of the diffuser 46.

The fan 64 provides for the drawing 102 of the principal flow of air. Meanwhile, the fan also draws the principal flow of air over the components in the electrical module 11. Accordingly, the cooling 116 is driven by the fan 64. Likewise, by passing through the fan 64, the bypass flow is compressed 118 to a certain much lesser extent by the fan 64. A pressure rise across the fan 64 is a result of the work put into the airflow by the fan 64. Thus, the fan 64 slightly compresses the flow of the bypass air.

Induction 120 by the pumps 40 draws air from the principal flow, typically upstream from the fan 64, into the diffuser 46. In certain embodiments, the flow may be drawn from an area downstream of the fan, thus providing additional pressure rise or a net higher gauge pressure as an output of the pumps 40.

Compression 118 by the pumps 40, or a single pump in certain embodiments, is completed before passing an output from the pumps 40 into the line 44. Typical operational capacities of the pumps may be about 1.7 PSI (12 kpa) gauge or pressure increase in the flow. Approximately 0.12 CFM (3.5 liters per minute) flow through the two pumps, and out the controlling orifice of the diffuser 46. A single pump will produce approximately the same pressure rise, but will reduce the volumetric flow rate to about 0.09 CFM (2.5 liters per minute). The compression 118 results in a flow of air that induces 120 or causes atomization.

Typically, the pumps 40 may compress air by about 1 to about 3 pounds per square inch (7 kpa to 21 kpa). However, it has been found that a set point of about 1.7 pounds per square inch (12 kpa) rise (gauge pressure above atmospheric) is appropriate through the pumps 40 to the nozzle 48 of the diffuser 46.

Typically, atomization 124 will occur by eduction, wherein the flow of compressed air over or near an opening drawing from the reservoir 52, will impart momentum to the fluid (liquid). This strips away liquid, thus drawing more liquid out of the tube, and atomizing 124 that liquid into a range of small particles. As a practical matter, in one embodiment, a feed line may receive a flow of comparatively higher speed air passing over the top thereof, thus stripping liquid from the feed line, and imparting a momentum transfer, with a corresponding draw in pressure. Thus, the liquid droplets are entrained within the air stream, thrown toward a nozzle cone, and ejected out a small aperture in the point of that cone against an opposite wall.

Atomization 124 as described is completed by an eductor. The eductor may operate in a classical concentrical, collinear, or parallel path arrangement. Alternatively, eduction may be done by one flow transverse to another, as described. The air flow thereby transferring momentum to the liquid available at a surface, is stripping droplets away from the surface. Movement of liquid calls for replacement liquid in the tube. The eductor may eject out a nozzle sized and shaped to match the plume of the eduction air flow.

Separation 126 may occur by various events. In one presently contemplated embodiment, the micro-cyclone 90 described hereinabove fits just above a nozzle, and receives liquid droplets entrained in the compressed airflow.

The micro-cyclone 90 typically requires a spiraling flow, flowing tangentially with respect to a radius and circumference of the diffuser 46. Meanwhile, the eductor operates to eject along a radius of the diffuser module 46 or the outer housing 46 of the diffuser module 45. Thus, the change in direction results in any large particles being thrown against an opposite wall by the eductor. Only the comparatively smaller particles remain with the air, pass up through the spiral path of the micro-cyclone 90. Moreover, the direct impact of droplets against an opposing wall results in an absolute and total change of direction. Change of direction should be at least 90 degrees, and will typically be closer to 180 degrees.

The momentum and energy transfer from the wall to the droplets may result in additional atomization of particles. The comparatively larger particles from this separation stage pass down through a passage into the reservoir 52 for recycling. Those that are sufficiently small to remain entrained pass into the micro-cyclone 90.

As described hereinabove, the micro-cyclone 90 then takes the droplets remaining in the airflow, and subjects them to centrifugal forces, thus throwing the comparatively larger particles of this distribution (size range) remaining in the entrained flow against the walls of the micro-cyclone channel 91. Subsequently droplets striking a solid surface coalesce and flow back down the sloping channel 91, into the reservoir 52 below.

Ultimately, only the comparatively smallest range of particles initially entrained in the airflow can eventually pass into and through the micro-cyclone 90, and past the gap between the dam 92 and a corresponding dam 92 in the nozzle 48.

Following atomization 124 as described, separation 126 in the diffuser 46 itself and later in the micro-cyclone 90 fixture inside the diffuser 46, as well as passing over the dam 92 through a narrow slot between the dam 92 and the micro-cyclone 90 and the dam 92 in the nozzle 48, the eduction 128 by the principal flow occurs. Eduction 128 occurs as the principal flow, flowing through the portion of the housing 12 that houses the diffuser module 45, passes by the nozzle 48, entraining the output of the nozzle 48.

The nozzle 48 may be any suitable shape, and may be straight, flat, tapered, non tapered, or the like. Typically, the eduction by the principal flow past the nozzle 48 further mixes and entrains the droplets and their carrier airstream from the pumps 40 into the shroud 56 toward the outlet 60 of the system 10. Following eduction 128, diffusion 130 occurs by momentum transfer between the flow of air proceeding from the nozzle 48, with its entrained droplets of the liquid from the reservoir 52, and the principal airflow. Eventually, the shroud 56 provides ducting 132 of the flow and the shroud 56 in combination with the louvers 58 provide directing 134 of that flow into the enclosed, habitable space. Again, a top cap on the shroud 56 may operate to impart a final change of direction, and may be tapered to facilitate a smoother turn by the airflow.

Ultimately, proper selection of a liquid for reservoir 52 to be used in the system 10 may result in antisepsis, disinfectant, extermination, fumigation, or germicidal activity by the fog or micro droplets themselves in the enclosed space. For example, various antibiotics, antiseptics, antimicrobial devices, and simply certain essential oils cause germicidal and fumigation activity in the enclosed space treated by the system 10.

In certain embodiments, the shroud 56 may be replaced with a conventional 90-degree elbow of polymeric, e.g., polyvinyl fluoride (PVC) pipe. The shroud 56 has been sized, such that the collar 15 will receive a pipe elbow that has been provided with an O-ring-type of cut in order that it may be captured by the collar 15. Thus, the system 10 may feed treated air directly through an elbow 56, rather than a shroud 56, into a heating, ventilating, and air conditioning (HVAC) system.

In certain embodiments, dual, silent pumps, as described in U.S. Pat. No. 8,047,813, incorporated hereinabove by reference, may be used in single or multiple arrangements.

A support 85 for mounting the pumps may be mounted on the rails 86 of the frame 81. A single pump 40 will provide an output of about 0.09 CFM (2.5 liters per minute) at about 1.7 PSI (12 kpa). In certain embodiment, a purchaser may purchase a system 10 absent two pumps 40, and use a single pump, with about two thirds the volume, and the same pressure for operation of the diffuser 46. Later, to improve capacity, an additional pump may be added to the system 10. Similarly, with the filtration module 19, improved filters may be included, and the fan 64 may be upgraded for a higher pressure differential. Thus, smaller mesh sizes may be used in the filtration 30, 32 with an upgrade in the power of the fan 64.

In some embodiments, the germicidal module 13 may be replaced with another or a different type of filter module 19. Thus, the expense of operation, as well as the expense of the module 13 may be eliminated if such a feature is deemed unnecessary. Thus, additional filtering, or no filtering, other than the original filter module 19 may be installed.

The fan system 64 is modular and may be changed out to alter power or volume flow rate capacity. The filter modules 19 may be swapped out, added, or changed. The germicidal module 13 may be eliminated, replaced with the filter module 19, or the like.

Similarly, at the opposite end of the system 10, the liquid reservoir 52 may be sized to fit virtually any practical demand. The adapters 50 may be selected to adapt to different sizes, manufacturers, or other sources of reservoirs 52, or the content liquid therein. Likewise, users may select their own reservoir 52 and fill according to their own bulk purchases of liquids. Thus, the system 10 is entirely modular at the behest of the user. In certain embodiments, the germicidal module 13 may be disabled in order to simply use the system 10 for its post-eduction germicidal and aroma effects of the diffuser 46. In other embodiments, the filter module 19 may still be absent or used as the first, last, only, combined filter. Thus, the initial filter 22 may suffice for a system 10 that is installed principally as a germicidal fogging machine to disperse or otherwise atomize a germicidal agent from the reservoir 52.

In certain embodiments, the micro-cyclone 90 may include a registration notch designed to register the micro-cyclone 90 in a plane of the flange 96. Thus, the flange 96 has a notch that registers, typically with the incoming pressurized line 44. Accordingly, this registration places the inlet or opening of the channel 91 above, but facing in the same direction as the injection or ejection nozzle feeding from the line 44.

The result is that the spray atomized from the initial eductor and nozzle must first proceed toward the opposite wall, internal wall, of the atomizer 46, change direction after smashing into the wall in the comparatively largest particles, and proceed along the wall in a circumferential direction in order to come back around at least 180 degrees. A design point is about 230 degrees to arrive at the opening to the channel 91. The atomized liquid droplets in the entrained pressurized air must travel forward to a wall, change direction by at least a 90 degree angle, proceed about 180 degrees around the circumference of the interior of the atomizer 46, rising to enter into the entrance of the channel 91.

Thus, a first stage separation occurs outside the nozzle 48 as comparatively large droplets coalesce against a film of oil or other liquid from the reservoir 52, collecting on the wall opposite the eductor inside the diffuser 46. A second stage separation occurs as the micro-cyclone 90 throws off the next smallest, comparatively larger particles still entrained in the compressed airflow during their transit through the micro-cyclone 90. The third stage of separation is the change in direction, and constriction of flow in passing over the dam 92 and through a slot between the dams 92 of the micro-cyclone 90 and the final eduction nozzle 48, in order to enter that nozzle 48.

Significantly, each of the first, second, and third separation processes operates in a significant length of less than an 0.4 inch (1 centimeter). Moreover, the shortest significant length for each is typically on the order of about one eighth inch, in the narrower dimension of the micro-cyclone 90 channel 91, and in the gap of about 0.060 inches (1.5 mm) between the dams 92 in the micro-cyclone 90 and the nozzle 48. Thus, each significant length, or maximum significant length of the various separation processes is successively smaller than its predecessor. From about 3/8 inch to about 1/8 inch by about 5/16 inch width and height dimensions on the channel 91, to a 0.06 inches (1.5 mm) gap on the final separator.

Moreover, each of the first, second, and third separation processes involves a change of direction. First, about 230 degrees, then a change of direction of about 330 degrees, and then two changes of direction, each of about 90 degrees, actually constituting a full change of 90 degrees to horizontal, followed by 90 degrees to vertical.

In a system 10 in accordance with the invention, the liquid in the reservoir 52 is not contaminated because the air drawn into the air pump has been purified, including all air through the fan 64, around the reservoir 52, and sent out into the room. Microbes, such as bacteria and viruses are eliminated before air reaches the compressor or fan. Thus, the system 10 may purify, filter, compress, diffuse, fan force, fumigate, in substantially any combination of such features.

Conventional systems recirculate liquids in ways that can contaminate their reservoirs. Here, only the comparatively smallest particles are discharged, those that remain airborne for from about one to about 30 minutes. Many will persist for an hour, and the minimum persistence time may be increased to five, ten, or twenty minutes. Only these smallest atomized particles leave the bottle, while the heavier particles recirculate. This is an even greater advantage if the liquid itself is not a germicide, wherein microbes could propagate.

Users may make an arbitrary selection of liquids, absent conventional contracts for proprietary liquids and cartridges, with captive customers and monopolistic profit margins. Any user or supplier may use the system 10, buy or sell any diffusable liquid, purchase or rent the diffusing system, buy or sell their own oils or other liquids, without being locked into a contract for any constituent of operation. Virtually any generic, refillable bottle may be used with any generic liquid suitable for atomizing.

The Air purifying industry may use the system 10 to add fragrance to pre-cleaned air, and may supply its own filter media. The Fragrance industry can use the system 10 to fill a room with a selected aromatic material without contamination over long term use. The essential oil industry can use the system to provide health benefits (e.g., like *eucalyptus* oil, citrus, etc.), a pleasant atmosphere, or aromatherapy for wellbeing. Agricultural enterprises can use it for animal husbandry, such as milking parlors, barns, poultry coops for chickens, turkeys, game hens, and the like, horse stables, and the like.

Individual patients may use it for respiratory care, such as asthma or allergy control, purifying air, adding therapeutic amounts of decongestants like *eucalyptus* or other liquids, distributing masking or germicidal aromas, or the like. In general the system may be controlled, programmed, or both, as described to deliver a therapeutic amount of a suitable liquid for any of the foregoing uses, at a rate selected for effectiveness, economy, safety, or other technical criterion. A user may select the liquid, the air flow rate (bulk or bypass volumetric flow rate), the diffusion rate (mass flow rate) of liquid atomized during operation, the wait time between diffusion operation, the operation time with each diffusion on-off cycle, as well as schedule and calendaring.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A system operable as a diffuser, the system comprising;
- a reservoir, operable to contain a liquid and defining axial, radial, and circumferential directions mutually orthogonal to one another;
- a first chamber and a second chamber separated by a wall therebetween as a barrier to flow directly therebetween in the axial direction;
- a nozzle operably connected to introduce into the first chamber a flow comprising droplets of the liquid, drawn from the reservoir, entrained in air; and
- a separator, comprising a channel, simultaneously progressing axially and circumferentially through the wall to conduct the flow from the first chamber into the second chamber.

2. The system of claim 1, wherein the channel is curved.

3. The system of claim 1 wherein the channel progresses in a spiral path through the wall.

4. The system of claim 1, wherein the channel comprises an entrance opening in the first chamber and an exit opening in the second chamber.

5. The system of claim 1, wherein the channel has a cross section of substantially constant area.

6. The system of claim 5, wherein the channel encloses a solitary, contiguous space, conducting all of the droplets.

7. The system of claim 1, wherein the channel comprises an entrance end in the first chamber and an exit end in the second chamber, the channel being shaped to pass comparatively smaller droplets with the flow out through the exit end, coalesce comparatively larger ones of the droplets against the channel as a recaptured liquid, and drain the recaptured liquid back to the reservoir.

8. The system of claim 1, wherein the nozzle forms a portion of an eductor.

9. The system of claim 1, comprising the nozzle operable as an atomizer connected to draw the liquid from the reservoir into the flow while injecting the flow into the first chamber.

10. The system of claim 1 wherein the channel is shaped to divide the droplets into comparatively larger droplets and comparatively smaller droplets by centripetal force on the flow by the channel.

11. The system of claim 1 wherein the channel curves through a first angle in a circumferential direction and a second angle in an axial direction.

12. The system of claim 11, wherein the channel has a cross sectional area that remains substantially constant between the first chamber and the second chamber.

13. The system of claim 1, comprising a pump as a source of the flow.

14. The system of claim 1, wherein the nozzle and a surrounding structure are shaped to draw the liquid from the reservoir in response to the flow through the nozzle.

15. The system of claim 1, comprising a motor, driving a pump, and a controller adjustable to control at least one of a duration of operation and a duration of deactivation between periods of operation of the motor.

16. The system of claim 1, wherein the separator and flow are coordinated to release droplets having an effective diameter of from about 1 micron to about 5 microns.

17. A system comprising:

a reservoir, shaped to contain a liquid providing a scent and to define axial, radial, and circumferential directions mutually orthogonal to one another;

an atomizer operably connected to draw the liquid from the reservoir and entrain the liquid as droplets into a flow of air;

a first chamber, a second chamber, a wall preventing direct contact therebetween, and a channel;

the channel, having an entrance in the first chamber, an exit in the second chamber, and a length therebetween greater than a distance directly between the first chamber and the second chamber;

the channel, operable as a separator of the droplets by progressing simultaneously in the axial direction and the circumferential direction in a shape effective to separate the droplets into comparatively smaller droplets carried into the second chamber with the flow and comparatively larger droplets coalesced as a recovered liquid passing back through the entrance toward the reservoir.

18. The system of claim 17, wherein the channel progresses uniformly at an angle in the axial direction along a majority of the length.

19. The system of claim 17, wherein the channel is shaped to have a substantially constant cross sectional area between the first chamber and the second chamber.

20. A system operable as a diffuser, the system comprising:

a reservoir to contain a liquid and define axial, radial, and circumferential directions;

a pump connected to provide a flow of air;

an atomizer, connected to draw a portion of the liquid from the reservoir, in response to the flow passing therethrough, divide the portion into droplets, and introduce the droplets into a first chamber;

the first chamber, a second chamber, and a wall therebetween, acting as a barrier against direct contact between the first chamber and the second chamber;

a channel, operable as a separator, having a length greater than a distance directly between the first and second chambers, and passing simultaneously radially and axially through the wall; and the channel, shaped to separate the droplets into comparatively smaller droplets passing with the flow into the second chamber and comparatively larger droplets coalescing and passing back into the first chamber.

* * * * *